(12) United States Patent
Abramson et al.

(10) Patent No.: US 8,017,401 B2
(45) Date of Patent: Sep. 13, 2011

(54) METHOD FOR DETERMINING REDOX ACTIVITY AND SCREENING COMPOUNDS BASED ON REDOX ACTIVITY

(75) Inventors: Jonathan J. Abramson, Beaverton, OR (US); Benjamin S. Marinov, Portland, OR (US)

(73) Assignee: State of Oregon acting by and through the State Board of Higher Education on behalf of Portland State University, Portland, OR (US)

( * ) Notice: Subject to any disclaimer, the term of this patent is extended or adjusted under 35 U.S.C. 154(b) by 532 days.

(21) Appl. No.: 11/884,051

(22) PCT Filed: Feb. 9, 2006

(86) PCT No.: PCT/US2006/004803
§ 371 (c)(1),
(2), (4) Date: Aug. 8, 2007

(87) PCT Pub. No.: WO2006/086670
PCT Pub. Date: Aug. 17, 2006

(65) Prior Publication Data
US 2008/0166814 A1    Jul. 10, 2008

Related U.S. Application Data

(63) Continuation-in-part of application No. 11/340,938, filed on Jan. 27, 2006, now abandoned.

(60) Provisional application No. 60/648,351, filed on Jan. 28, 2005, provisional application No. 60/651,730, filed on Feb. 9, 2005.

(51) Int. Cl.
*G01N 31/00*    (2006.01)

(52) U.S. Cl. .............................. 436/2; 436/172; 436/164
(58) Field of Classification Search .................. None
See application file for complete search history.

(56) References Cited

U.S. PATENT DOCUMENTS

| 4,233,402 A | | 11/1980 | Maggio et al. |
| 5,340,716 A | | 8/1994 | Ullman et al. |
| 6,060,324 A | * | 5/2000 | Naguib ........................ 436/71 |
| 6,114,177 A | * | 9/2000 | Naguib ....................... 436/172 |

(Continued)

OTHER PUBLICATIONS

Marinov, B. S. et al. "Estimation of redox properties of chemical compounds by their reactions with free radicals." Analytical Biochemistry (1994) 220 p. 154-159.*

(Continued)

*Primary Examiner* — Yelena G Gakh
*Assistant Examiner* — Christopher A Hixson
(74) *Attorney, Agent, or Firm* — Klarquist Sparkman, LLP

(57) ABSTRACT

A method for identifying the redox activity of a subject compound is disclosed. The method can be performed aerobically and can include forming a mixture comprising a free-radical precursor and a compound to be tested, and converting the free-radical precursor into a free-radical anion and a free-radical cation. After the free radical cation and the free radical anion have been formed, the relative redox activity of the subject compound may cause a difference in the rate of photobleaching of the mixture and/or the rate of superoxide generation. These differences can be quantified and used to identify the redox activity of the subject compound. This sensitive technique for measuring redox activity can be used to screen compounds for various biological applications. Drugs also can be developed based on the relationship between redox activity and biological activity for particular biological applications.

18 Claims, 9 Drawing Sheets

U.S. PATENT DOCUMENTS

2003/0219443 A1    11/2003  Lee et al.

OTHER PUBLICATIONS

Beauchamp, Charles et al. "Superoxide dismutase: improved assays and an assay applicable to acrylamide gels." Analytical Biochemistry (1971) 44 p. 276-287.*

Benov, Ludmil et al. "Is reduction of the sulfonated tetrazolium 2,3-bis (2-methoxy-4-nitro-5-sulfophenyl)-2-tetrazolium 5-carboxanilide a reliable measure of intracellular superoxide production?" Analytical Biochemistry (2002) 310 p. 186-190.*

Ellis, Holly R. et al. "Novel application of 7-chloro-4-nitrobenzo-2-oxa-1,3-diazole to identify cysteine sulfenic acid in the AhpC component of alkyl hydroperoxide reductase." Biochemistry (1997) 36 p. 15013-15018.*

Marinov, B. S. et al. "Redox properties of benzocaine and its homologs." Membrane and Cell Biology (1997) 11 507-513.*

Marinov, B. S. et al. "Redox properties of local anesthetics: A structural determination of closed channel blockers in BTX-modified Na+ channels." Membrane and Cell Biology (2001) 14 553-563.*

Bryk et al., "Peroxynitrite reductase activity of bacterial peroxiredoxins," *Nature* 407:211-215, 2000.

Carballal et al., "Sulfenic Acid Formation in Human Serum Albumin by Hydrogen Peroxide and Peroxynitrite," *Biochemistry* 42:9906-9914, 2003.

Kutala et al., "Reaction of superoxide with trityl radical: implications for the determination of superoxide by spectrophotometry," *Archives of Biochemistry and Biophysics* 424:81-88, 2004.

Molecular Probes, Product Information, Oct. 12, 2004, "MitoSOX™ Red Mitochondrial superoxide indicator *for live-cell imaging* (M36008)".

Roubaud et al., "Quantitative Measurement of Superoxide Generation Using the Spin Trap 5-(Diethoxyphosphoryl)-5-methyl-l-pyrroline-N-oxide," *Analytical Biochemistry* 247:404-411, 1997.

Zimmerman, "Sulfenic Acids: An Overview," *Free Radical and Radiation Biology Program*, pp. 1-10, The University of Iowa, Iowa City, Iowa, Spring 2003 Term, 2003.

Aboderin, A.A. and Boedefeld, E., "Reaction of Chicken Egg White Lysozyme with 7-chloro-4-nitrobenz-2-oxa-1,3-diazole. II. Sites of Modification." *Biochim. Biophys. Acta*, 420(1): 177-186 (1976).

Abramson, J.J., et al., "Mechanism of Anthraquinone-Induced Calcium Release from Skeletal Muscle Sarcoplasmic Reticulum." *J. Biol. Chem.*, 263(35): 18750-18758 (1988).

Benov, L. and Fridovich, I., "Is Reduction of the Sulfonated Tetrazolium 2,3-bis(2-methoxy-4-nitro-5-sulfophenyl)-2-tetrazolium-5-carboxanilide a Reliable Measure of Intracellular Superoxide Production?" *Anal. Biochem.*, 310(2): 186-190 (2002).

Carballal, S., et al., "Sulfenic Acid Formation in Human Serum Albumin by Hydrogen Peroxide and Peroxynitrite," *Biochemistry*, 42(33): 9906-9914 (2003).

Cassina, A.M., et al., "Cytochrome C Nitration by Peroxynitrite," *J. Biol. Chem.* 275(28): 21409-21415 (2000).

Dambrova, M., et al., "Improved Method for EPR Detection of DEPMPO-Superoxide Radicals by Liquid Nitrogen Freezing," *Biochem. Biophys. Res. Commun.*, 275(3): 895-898 (2000).

El Emam, A.A., et al., "Determination of Lisinopril in Dosage Forms and Spiked Human Plasma Through Derivatization with 7-chloro-4-nitrobenzo-2-oxa-1,3-diazole (NBD-C1) Followed by Spectrophotometry or HPLC with Fluorimetric Detection," *J. Pharm. Biomed. Anal.*, 34(1): 35-44 (2004).

Ellis, H.R. and Poole, L.B., "Novel Application of 7-chloro-4-nitrobenzo-2-oxa-1,3-diazole to Identify Cysteine Sulfenic Acid in the AhpC Component of Alkyl Hydroperoxide Reductase," *Biochemistry*, 36(48): 15013-15018 (1997).

Gill, A., et al., "Pharmacology of Bepridil," *Am. J. Cardiol.*, 69(11):11D-16D (1992), abstract only.

Golfetti, R., et al., "Chronically Administered Acetaminophen and the Ischemia/Reperfused Myocardium," *Exp. Biol. Med.*, (Maywood) 228(6): 674-682 (2003).

Grigoriev, S.M., et al., "Regulation of Mitochondrial KATP Channel by Redox Agents," *Biochim. Biophys Acta*, 1410(1): 91-96 (1999).

Honen, B.N., et al., "Suppression of Calcium Sparks in Rat Ventricular Myocytes and Direct Inhibition of Sheep Cardiac RyR Channels by EPA, DHA and Oleic Acid," *J. Membr. Biol.*, 196(2): 95-103 (2003).

Jiang, M. and Zhang, J., "Water Stress-Induced Abscisic Acid Accumulation Triggers the Increased Generation of Reactive Oxygen Species and Up-Regulates the Activities of Antioxidant Enzymes in Maize Leaves," *J. Exp. Bot.*, 53(379): 2401-2410 (2002).

Kelm, M., et al., "The Nitric Oxide/Superoxide Assay. Insights into the Biological Chemistry of the NO/O-2. Interaction," *J. Biol. Chem.*, 272(15): 9922-9932 (1997).

MacLennan, D.H., "Purification and Properties of an Adenosine Triphosphatase from Sarcoplasmic Reticulum," *J. Biol. Chem.*, 245(17): 4508-4518 (1970).

Marinov, B.S. and Evtodienko, J.V, "Estimation of Redox Properties of Chemical Compounds by Their Reactions with Free Radicals," *Anal. Biochem.*, 220(1): 154-159 (1994).

Marinov, B.S. and Saxon, M.E., "Dihydropyridine $Ca^{2+}$ Agonists and Channel Blockers Interact in Opposite Manner with Photogenerated Unpaired Electrons," *Febs Lett.*, 186(2): 251-254 (1985).

Marinov, B.S., "$Na^+$-Channel Antagonists Act as Electron Donors While Agonists Act as Electron Acceptors in Reaction with Dye Free Radicals," *Febs Lett.*, 191(1): 159-162 (1985).

Marinov, B.S., "Norepinephrine with its Precursors and their Antagonists Haloperidol and Phentolamine Interact with Dye Free Radicals in Opposite Ways," *Febs Lett.*, 198(1): 130-134 (1986).

Olojo, R.O., et al., "Spectrophotometric and fluorometric assay of superoxide ion using 4-chloro-7-nitrobenzo-2-oxa-1,3-diazole," *Analytical Biochem.*, 339: 338-344 (2005).

Price, N.C., et al., "Fluorescent and Spin Label Probes of the Environments of the Sulfhydryl Groups of Porcine Muscle Adenylate Kinase," *J. Biol. Chem.*, 250(2): 644-652 (1975).

Quan, C., et al., "Use-Dependent Inhibition of Na+ Currents by Benzocaine Homologs," *Biophys. J.*, 70(1): 194-201 (1996).

Roubaud, V., et al., "Quantitative Measurement of Superoxide Generation Using the Spin Trap 5-(diethoxyphosphoryl)-5-methyl-1-pyrroline-N-oxide," *Anal. Biochem.*, 247(2): 404-411 (1997).

Sanders, S.P., et al., "A Comparative Study of EPR Spin Trapping and Cytochrome C Reduction Techniques for the Measurement of Superoxide Anions," *Free Radic. Biol. Med.*, 16(6): 753-761 (1994).

Sato T., et al., "Bepridil, an Antiarrhythmic Drug, Opens Mitochondrial KATP Channels, Blocks Sarcolemmal KATP Channels, and Confers Cardioprotection," *J. Pharmacol. Exp. Ther.*, 316: 182-188 (2006).

Staniek, K. and Nohl, H., "$H(2)O(2)$ Detection from Intact Mitochondria as a Measure for One-Electron Reduction of Dioxygen Requires a Non-Invasive Assay System," *Biochim. Biophys. Acta*, 1413(2): 70-80 (1999).

Stark, U., et al., "Rate-Dependent Effects of Detajmium and Propafenone on Ventricular Conduction and Refractoriness in Isolated Guinea Pig Hearts," *J. Cardiovasc. Pharmacol.*, 27(1): 125-131 (1996).

Stuchbury, T., et al., "A Reporter Group Delivery System with Both Absolute and Selective Specificity for Thiol Groups and an Improved Fluorescent Probe Containing the 7-nitrobenzo-2-oxa-1,3-diazole Moiety," *Biochem. J.*, 151(2): 417-432 (1975).

Sutherland, M.W., and Learmonth, B.A., "The Tetrazolium Dyes MTS and XTT Provide New Quantitative Assays for Superoxide and Superoxide Dismutase," *Free Radic. Res.*, 27(3): 283-289 (1997).

Taha, E.A., "Kinetic Spectrophotometric Methods for the Determination of Dothiepin Hydrochloride in Bulk and in Drug Formulation," *Anal. Bioanal. Chem.*, 376(7): 1131-1136 (2003).

Tarpey, M.M. and Fridovich, I., "Methods of Detection of Vascular Reactive Species: Nitric Oxide, Superoxide, Hydrogen Peroxide, and Peroxynitrite," *Circ. Res.*, 89(3): 224-236 (2001).

Thomson, L., et al., "Kinetics of Cytochrome C2+ Oxidation by Peroxynitrite: Implications for Superoxide Measurements in Nitric Oxide-Producing Biological Systems," *Arch. Biochem. Biophys.*, 319(2): 491-497 (1995).

Valdivia, H.H., et al., "Direct Binding of Verapamil to the Ryanodine Receptor Channel of Sarcoplasmic Reticulum," *Biophys J.*, 58(2): 471-481 (1990).

Valgimigli, L., et al., "Measurement of Oxidative Stress in Human Liver by EPR Spin-Probe Technique," *Free Radic. Res.*, 33(2): 167-178 (2000).

Valgimigli, M., et al., "Oxidative Stress EPR Measurement in Human Liver by Radical-Probe Technique. Correlation with Etiology, Histology and Cell Proliferation," *Free Radic. Res.*, 36(9): 939-948 (2002).

Vasquez-Vivar, J., et al., "Mitochondrial Aconitase is a Source of Hydroxyl Radical. An Electron Spin Resonance Investigation," *J. Biol. Chem.*, 275(19): 14064-14069 (2000).

Xia, R., et al., "Skeletal Muscle Sarcoplasmic Reticulum Contains a NADH-Dependent Oxidase that Generates Superoxide," *Am. J. Physiol Cell Physiol*, 285(1): C215-C221 (2003).

Xu, L., et al., "Effects of Local Anesthetics on Single Channel Behavior of Skeletal Muscle Calcium Release Channel," *J. Gen. Physiol.*, 101(2): 207-233 (1993).

\* cited by examiner

METHOD FOR DETERMINING REDOX ACTIVITY AND SCREENING COMPOUNDS BASED ON REDOX ACTIVITY

CROSS REFERENCE TO RELATED APPLICATION

This is the U.S. National Stage of International Application No. PCT/US2006/004803, filed Feb. 9, 2006, which was published in English under PCT Article 21(2), which is a continuation-in-part of prior U.S. patent application titled "Detection of Superoxide Ions," filed Jan. 27, 2006, having the inventors Jonathan J. Abramson and Rotimi O. Olojo, which has been assigned Application No. 11/340,938, currently pending, which claims the benefit of the earlier filing date of U.S. Provisional Application No. 60/648,351, filed Jan. 28, 2005, now abandoned. This application also claims the benefit of the earlier filing date of U.S. Provisional Application No. 60/651,730, filed Feb. 9, 2005. Prior U.S. patent application titled "Detection of Superoxide Ions," filed Jan. 27, 2006, having the inventors Jonathan J. Abramson and Rotimi O. Olojo, which has been assigned Application No. 11/340,938, U.S. Provisional Application No. 60/648,351, U.S. Provisional Application No. 60/651,730, and International Application No. PCT/US2006/004803 are incorporated herein by reference.

STATEMENT OF GOVERNMENT SUPPORT

This invention was made with government support from the National Institutes of Health; contract number R01 AR 48911. The government has certain rights in the invention.

FIELD

This disclosure relates generally to determining the redox activity of compounds and/or to applying information concerning redox activity, such as for screening compounds and/or for developing drugs.

BACKGROUND

The traditional approach to drug development involves the identification of a target and the empirical testing of a group of compounds for their activity relative to that target. The group of compounds selected for empirical testing often is very large. For example, the group may include tens of thousands of individual compounds. In some cases the group is limited to modifications of an existing drug or is otherwise narrowed based on what is known about the chemical structure of the target. Eventually, most of the compounds are eliminated and a small group of compounds passes to later stages of the development process, such as to clinical trials.

The cost of empirically testing thousands of compounds can be very high. Furthermore, there is a growing body of information about the chemical mechanisms behind drug activity. Thus, there is a trend toward rational drug design, which involves using known information to narrow the group of candidate compounds and thereby lower the cost of empirical screening. In rare cases, enough information is known to design specific chemical structures with the desired biological activity.

Greater knowledge about what chemical properties cause compounds to interact in various ways with biological structures will facilitate rational drug design. Redox potential is an example of a chemical property that may be of interest for its effect on biological activity. For example, Marinov, B. S., et al., "Redox Properties of Local Anesthetics: A Structural Determination of Closed Channel Blockers in BTX-Modified $Na^+$ Channels," MEMBER CELL BIOL. 14(4):553-63 (2001) (Marinov) provides evidence that the "redox properties of tetracaine, benzocaine, and their homologs correlate with their ability to enhance $Na^+$ channel inactivation in BTX-modified $Na^+$ channels."

Knowledge about how certain chemical properties affect biological activity only is useful if compounds having such properties can be readily identified. Existing techniques for measuring redox activity are limited. For example, cyclic voltammetry (an electrochemical method) has been used to evaluate the redox properties of compounds by monitoring the exchange of electrons between the compounds and electrodes in solution. This method usually requires relatively large concentrations of the subject compound, which may be difficult to obtain. Moreover, many weak redox-active compounds do not directly exchange electrons with an electrode. Weak redox-active compounds also cannot be detected with certain conventional chemical probes, such as cytochrome C and dithionitrobenzoate.

Marinov describes testing the redox properties of local anesthetics by their "ability to donate electrons to radical intermediates of eosin dye excited by visible light." This method is limited, however, at least in part because it involves testing under anaerobic conditions. Alternative methods for evaluating the redox properties of compounds are needed.

SUMMARY

Disclosed herein are embodiments of a method for identifying the redox activity of a subject compound. These embodiments can be performed aerobically. The subject compound can be, for example, a drug candidate. Some of the disclosed embodiments include forming a mixture comprising a free-radical precursor and the subject compound and converting the free-radical precursor into a free-radical anion and a free-radical cation, such as by exposing the free-radical precursor to light. If the subject compound is an electron acceptor, an initial electron donor also can be added to donate an electron to the free-radical cation. After the free-radical cation and the free-radical anion have been formed, the relative redox activity of the subject compound may cause a difference in the rate of photo-bleaching of the mixture and/or the rate of superoxide generation. These differences can be used to identify the redox activity of the subject compound. In some embodiments, a biological activity of the subject compound is then identified based on its redox activity.

In embodiments that include measuring the concentration of superoxide in the mixture, the mixture may include a superoxide detection molecule that reacts with superoxide to form a detectable product. The concentration of the detectable product can be measured, for example, by measuring light absorbance at a wavelength absorbed by the detectable product or light fluorescence at a wavelength emitted by the detectable product. The superoxide detection molecule can be, for example, NBD-Cl or XTT. In these embodiments, the concentration of the detectable product can be measured by measuring light absorbance at a wavelength of about 470 nm. If the superoxide detection molecule is NBD-Cl, the concentration of the detectable product also can be measured by measuring the fluorescence at an excitation a wavelength of about 470 nm and at an emission wavelength of about 550 nm. If the superoxide detection molecule is NBD-Cl, the concentration of NBD-Cl in the mixture prior to reaction with superoxide can be, for example, between about 30 μM and about 500 μM.

In addition to or in place of measuring the concentration of superoxide, the concentration of the free-radical precursor, the free-radical anion and/or the free-radical cation can be measured. The concentration of the free-radical precursor can be measured, for example, by measuring light absorbance by the mixture at a wavelength absorbed by the free-radical precursor. The free-radical precursor may, for example, be a dye that bleaches by reaction of two free-radical anion molecules. Such dyes include eosin, erythrosin and methylene blue. If the subject compound affects the concentration of the free-radical anion, such as by donating an electron to the free-radical cation or by accepting an electron from the free-radical anion, monitoring the rate at which the dye bleaches can be used as a measurement of the redox activity of the subject compound.

Some embodiments of the disclosed method are directed to selecting a compound for a biological application. These embodiments can include, for example, screening a plurality of compounds based on redox activity and selecting a compound for a biological application based at least in part on the compound's redox activity and a correlation between redox activity and biological activity for the biological application. The compounds can be screened for redox activity using an embodiment of the disclosed method for identifying the redox activity of a subject compound. The biological application can be, for example, a biological application involving interaction between a compound and a particular biological structure, such as a membrane-bound transport protein.

Some embodiments of the disclosed method can be used to developing drugs. For example, a redox activity corresponding to improved biological activity can be identified for compounds interacting with a particular biological structure, such as a membrane-bound transport protein. Using this information, a drug can be designed to have the desired redox activity. Designing the drug can include adding or removing at least one functional group to or from the drug. If the desired redox activity is increased electron donor capability, adding or removing at least one functional group may be used to increase the electron donor capability of the drug. Similarly, if the desired redox activity is increased electron acceptor capability, adding or removing at least one functional group may be used to increase the electron acceptor capability of the drug.

DETAILED DESCRIPTION

Figure 1:
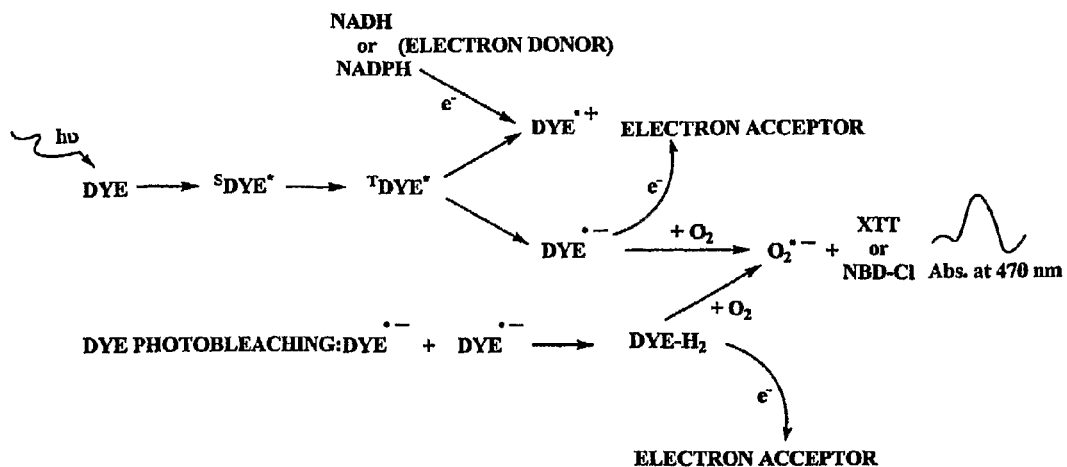
FIG. 1 is an illustration of a possible mechanism for certain embodiments of the disclosed method for measuring the redox activity of a compound.

Unless otherwise explained, all technical and scientific terms used herein have the same meaning as commonly understood by one of ordinary skill in the art to which this disclosure belongs. The singular terms "a," "an," and "the" include plural referents unless the context clearly indicates otherwise. Similarly, the word "or" is intended to include "and" unless the context clearly indicates otherwise. The term "includes" means "comprises." The separations described herein can be partial, substantial or complete separations unless indicated otherwise. All percentages recited herein are weight percentages unless indicated otherwise. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

The following terms may be abbreviated in this disclosure as follows: adenosine 5'-triphosphate (ATP), dimethyl sulfoxide (DMSO), ethylenediaminetetraacetic acid (EDTA), electron paramagnetic resonance (EPR), DL-glyceraldehyde (GA), glycolaldehyde (GLA), nicotinamide adenine dinucleotide reduced form (NADH), nicotinamide adenine dinucleotide phosphate reduced form (NADPH), 4-chloro-7-nitrobenzo-2-oxa-1,3-diazole (NBD-Cl), nitroblue tetrazolium (NBT), sarcoplasmic reticulum (SR), superoxide dismutase (SOD), 2-amino-2(hydroxymethyl)-1,3-propanediol, hydrochloride (Tris-HCl), and 2,3-bis(2-methoxy-4-nitro-5-sulphophenyl)-5-[(phenylamino)carbonyl]-2H-tetrazolium hydroxide (XTT).

Disclosed herein are embodiments of a method for gathering and/or applying information concerning the redox activity of compounds. This information can be used, for example, in the selection of compounds for a biological application and/or in the development of drugs. Some disclosed embodiments are performed aerobically and involve a reaction between the subject compound and a free radical. Due to the high reactivity of free radicals, these embodiments are capable of detecting even weak redox activity.

It is known that the conformational properties of a compound affect its biological activity. Conventionally, it was thought that the conformational changes caused by binding a drug to a target protein were responsible for changes in the properties of the target protein. Conformational properties are indeed important for promoting interaction between a drug and a target protein. However, once a drug is bound to a target protein, the drug's redox activity may be the key factor causing functional changes to occur in the target protein. For example, it is possible for a large group of compounds to have structural properties that allow them to bind to a target protein. Among these compounds, their redox activity may affect their biological activity more than differences in how they bind to and change the conformation of the target protein.

The effect of redox activity on biological activity has been shown, for example, in tests performed on drugs that interact with membrane-bound transport proteins. These proteins have been shown to be either activated or inhibited by drugs that are either electron donors or electron acceptors. For example, nifedipine, verapamil and diltiazem, which are inhibitors of the L-type calcium channel, are electron donors, while L-type calcium channel activators are electron acceptors (see reference 1). Similarly, local anesthetics, anti-arrhythmics and some anti-convulsants, which act as sodium channel inhibitors, are electron donors, while cardiotonic drugs that enhance sodium transport into cells are electron acceptors (see reference 2). The mitochondrial ATP-dependent potassium channel is activated by the electron donor diethyl benzocaine and inhibited by the electron acceptor pelargonidine (see reference 3). In another example, ryanodine, caffeine, doxorubicin, mitoxantrone, cystine, glutathione disulfide and diamide, which are activators of the sarcoplasmic reticulum calcium release channel, are electron acceptors, while tetracaine, procaine, docohexaenoic acid, glutathione and cysteine, which are inhibitors of the sarcoplasmic reticulum calcium release channel, are electron donors. Additional, consistent results were found with activators and inhibitors of the beta-receptor (see reference 4) and with regulators of oxygen affinity to hemoglobin (see reference 5).

Since redox activity affects biological activity, it can be used as a tool for screening and/or designing drugs. Most of the compounds discussed above have relatively weak redox activity. The correlation, however, between redox activity and activation or inhibition of a target protein indicates that proteins are sensitive to subtle differences in redox activity. Thus, in order to apply redox activity as a useful tool for screening and/or designing drugs, there must be a method to identify the weak redox activity of compounds with enough accuracy to detect subtle differences. Most conventional methods for analyzing redox activity are incapable of detecting the activity of weak electron donors and acceptors. Other methods are impractical. For example, as discussed above, some methods require deaeration of the solution being tested. These and other methods also may require flash photolysis techniques for analyzing free-radical lifetime (see reference 6). Both deaeration and flash photolysis are relatively expensive and time consuming.

Disclosed herein are embodiments of a method for detecting subtle differences in redox activity. For example, some disclosed embodiments are capable of detecting the redox properties of compounds that cannot be accurately measured by conventional cyclic voltammetry techniques. Some of the disclosed embodiments can be performed without the need for deaeration and/or flash photolysis. For example, some of the disclosed embodiments can be performed in a standard oxygen-containing atmosphere. Rather than eliminating oxygen, oxygen can be incorporated into the method as a quantifiable electron acceptor.

Some of the disclosed embodiments rely on bleaching and/or the formation of superoxide in the solution being tested as an indicator of redox activity. A possible mechanism is diagramed in FIG. 1. This mechanism is theoretical only, and not intended to limit the scope of the invention. The process can begin with a mixture of a free-radical precursor (shown as "dye" in FIG. 1) and a subject compound. An initial electron donor (shown as "NADH or NADPH" in FIG. 1) also can be added if the subject compound is an electron acceptor. As shown in FIG. 1, the free-radical precursor first can be converted into a free-radical anion and a free-radical cation. One method for forming the free-radical anion and the free-radical cation is by application of light, often from a light source at a wavelength and/or a period of time sufficient to generate the free-radical anion and the free-radical cation. The free-radical anion and free-radical cation are highly reactive and have a tendency to recombine to eliminate their charge. Their reactivity also allows them to exchange electrons with relatively weak electron donors and acceptors. If the free-radical cation reacts with an electron donor other than the free radical anion, the concentration of the free-radical cation decreases, thereby increasing the lifetime of the free-radical anion. Stabilized in this way, the free radical anion can react with itself, which may cause detectable bleaching, or may react with oxygen in the solution to form superoxide.

If the subject compound is an electron donor, it can react with the free-radical cation to increase the stability of the free-radical anion and thereby increase the detectable bleaching and/or the concentration of superoxide. Thus, a greater electron donor activity in the subject compound correlates with a greater degree of bleaching and/or a greater superoxide concentration. If the subject compound is an electron acceptor, a separate initial electron donor can be added to react with the free-radical cation and thereby initially stabilize the free-radical anion. The subject compound then can accept an electron from the free-radical anion or from the free-radical anion pair (which also can react with oxygen to form superoxide), thereby decreasing the detectable bleaching and/or the superoxide concentration.

The two variables that may be affected by the redox properties of the subject compound are bleaching caused by reaction of the free-radical anion with itself and the formation of superoxide caused by reaction of the free-radical anion or free-radical anion pair with oxygen. Each of these variables can be measured with a high degree of accuracy. Bleaching can be monitored, for example, with a spectrophotometer. The superoxide concentration can be monitored, for example, by introducing a superoxide detection molecule that reacts with superoxide to form a detectable product. The superoxide detection molecule may change its absorption and/or fluorescence characteristics upon interacting with superoxide. These changes can monitored with a spectrophotometer, a fluorimeter or some other detection method.

Embodiments of the disclosed method are capable of detecting redox activity with a high degree of sensitivity. The information gathered by performing embodiments of the disclosed method can be translated into quantitative values. For example, the rate of increase or decrease in absorption can be measured for several samples with known levels of redox activity. The resulting data then can be used to develop an equation representing the relationship between rate of increase or decrease in absorption and redox activity for a given set of conditions. Alternatively, redox activity can be evaluated by comparison. For example, a significant number of compounds can be evaluated using standardized conditions and the resulting rates of increase or decrease in absorption can be cataloged for comparison. The standardized conditions can include, for example, a standard concentration of the subject compound, a standard type and concentration of dye, a standard type of buffer, etc. Once enough compounds are catalogued, the existing data can serve as a scale for evaluating the relative redox activity of newly tested compounds.

As discussed above, some embodiments of the disclosed method include detecting the concentration of superoxide. Conventional methods that can be used for this purpose include, for example, EPR spin trapping (see references 7-9), spectrophotometry using cytochrome C (see reference 10), spectrophotometry using nitro-substituted aromatics (e.g., nitroblue tetrazolium) (see reference 11), and electrochemical detection using SOD-immobilized microelectrodes. Any of these techniques can be used to detect the superoxide generated in embodiments of the disclosed method. Several of these techniques, however, have limited sensitivity and/or specificity. For example, many reduced forms of redox-active compounds are capable of reducing cytochrome C (see references 12-13). Similarly, measuring superoxide concentration with nitroblue tetrazolium can yield erroneous results when measurements are taken under aerobic conditions (see reference 14).

In some embodiments, a superoxide detection molecule is used having the following structure:

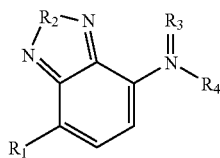

wherein $R_1$ is a halogen and $R_2$, $R_3$ and $R_4$ each are either oxygen or sulfur. For example, the superoxide detection molecule can be 4-chloro-7-nitrobenzo-2-oxa-1,3-diazole (NBD-Cl), which has the following structure:

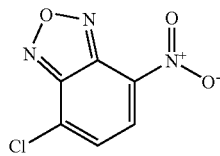

Another useful superoxide detection molecule is 2,3-bis(2-methoxy-4-nitro-5-sulfophenyl)-2H-tetrazolium-5-carboxanilide (XTT) (see reference 15). Combinations of superoxide detection molecules also can be used to practice the disclosed embodiments.

Among superoxide detection molecules, NBD-Cl and XTT have been shown to be particularly well-suited for use in disclosed embodiments. NBD-Cl previously has been used for the fluorescent detection of reactive thiols (see references 16-18) as well as primary and secondary amines (see reference 19). NBD-Cl also has been used to quantify the concentration of the antidepressant dothiepin hydrochloride (see reference 20) and as a derivatizing agent for lisinopril, a synthetic peptide anti-hypertensive drug (see reference 21).

In embodiments of the disclosed method, NBD-Cl can be used with either spectrophotometric or fluorimetric techniques. Upon excitation at 470 nm, the product of the reaction of NBD-Cl and superoxide fluoresces at 550 nm. As shown in Example 8 below, NBD-Cl is able to distinguish superoxide from other reactive oxygen species. It does not appear to be sensitive to commonly generated reactive oxygen species other than superoxide. The product of reaction of NBD-Cl and superoxide also exhibits a linear correlation between absorbance and superoxide concentration (at least in the range of 2 to 200 µM).

NBD-Cl as a superoxide-detection molecule has utility beyond embodiments of the disclosed method for measuring the redox activity of compounds. The detection and measurement of superoxide has been critical to the understanding of several biological events such as aging, muscle fatigue, ischemia-reperfusion and inflammation in living organisms (see references 22-24). During such biological events, as well as during metabolism and aging, levels of superoxide typically are elevated. As a consequence, levels of peroxide, hydroxyl radicals and other reactive oxygen species also increase. These elevated levels of reactive oxygen species appear to functionally alter numerous biological transport proteins and the integrity of biological membranes. Vascular dysfunction, as observed in atherosclerosis, hypertension, diabetes and postischemic myocardium, has been suspected as a consequence of alterations in both the rates of formation and the rates of scavenging of superoxide (see reference 25).

As discussed above, some embodiments of the disclosed method include forming a mixture comprising a free-radical precursor and a subject compound. These components can be present in a solution that is aerobic due to exposure to air. The free-radical precursor can be present at a concentration, for example, between about 1 µM and about 15 µM, such as between about 5 µM and about 10 µM. The subject compound can be present at a concentration, for example, between about 0.1 µM and about 10 mM, such as between about 100 µM and about 200 µM. In embodiments that include the detection of superoxide, a superoxide-detection molecule can be present at a concentration, for example, between about 10 µM and about 500 µM, such as between about 40 µM and about 60 µM. If the subject compound is an electron acceptor, an initial electron donor can be present at a concentration, for example, between about 10 µM and about 1 mM, such as between about 50 µM and about 150 µM.

Once the redox activity has been determined for a certain compound, it can be used to identify a level of biological activity for the compound. For example, when a new compound is screened for activity at the L-type calcium channel, the relative activity of the compound at the L-type calcium channel can be determined based on its redox activity. This is possible because it is known that inhibitors of the L-type calcium channel are electron donors and activators of the L-type calcium channel are electron acceptors, as discussed above. There is a direct relationship between the level of redox activity and the level of biological activity, as shown for example in Example 3 below. Thus, the relative strength of the compound's redox activity can be correlated with its level of biological activity.

The effect of the redox activity of compounds interacting with a particular biological protein can be determined by testing the redox activity of compounds that have known effects on protein function. For example, known activators and inhibitors of the protein can be tested. If it is found that all compounds with one effect (e.g., all activators) are electron donors and all compounds with the opposite effect (e.g., all inhibitors) are electron acceptors, it can be deduced that a redox reaction is at least partially responsible for the effect of the compounds on the protein. Redox activity then can be used to screen other compounds for their effect on the protein. Redox activity also can be used to design new drugs. For example, the redox activity of a compound known to interact with a protein can be modified to create, change or enhance its effect on the protein.

Drugs can be designed to have a desired redox activity using conventional chemical synthesis techniques. To enhance the electron donor capability of a compound a functional group can be added that increases electron donor capability. Similarly, to enhance the electron acceptor capability of a compound a functional group can be added that increases electron acceptor capability. Functional groups known to increase electron donor capability include groups that can donate an electron pair, for example, chalcogen-containing groups, such as hydroxy, alkoxy, sulfhydryl, sulfide and selenide. Other electron pair donating groups include nitrogen-containing groups, such as optionally substituted amino groups, hydrazines and the like. Other examples of groups that enhance electron donating ability include electropositive groups, which may work through non-resonance effects. Examples of such electropositive groups include silyl groups. Still other functional groups that increase electron donor capability include saturated and unsaturated groups, such as alkyl, alkenyl, aryl, and alkynyl moieties, which can increase electron donor capabilities via both resonance and non-resonance effects. Functional groups known to increase electron acceptor capability include electrophilic groups, which may be conjugated or not conjugated with the core drug molecule. Suitable examples include, without limitation, nitro groups, cyano groups, acyl groups, phosphoryl groups, sulfuryl groups, halides and haloalkyl groups, for example trifluoromethyl groups. Such functional groups can be added as is known to those of skill in the art of organic synthesis employing techniques including, for example, those described in March, J.; Smith, M. B. *March's Organic Chemistry: Reactions, Mechanism and Structure* 5th ed.; Wiley & Sons: New York, 2001. The redox activity of compounds also can be modified by removing functional groups. This can be accomplished as is known to those of skill in the art via, for example, the techniques described in March's Organic Chemistry.

EXAMPLES

The following examples are provided to illustrate certain particular embodiments of the disclosure. Additional embodiments not limited to the particular features described are consistent with the following examples.

Example 1

Measuring Redox Properties of Compounds

A sample buffer containing a compound to be tested and a photo-reactive dye (i.e., 10 µM methylene blue, eosin B or erythrosin B) can be continuously illuminated with white light (e.g., about 10 cm away from a halogen 20 W light source) and its spectral characteristics monitored as a function of time (e.g., using a HP8452A diode array spectrophotometer). This can be performed in the presence of oxygen. In general, oxygen dissolved in the solution may decrease the photochemical activity of the dye. To compensate and to increase the sensitivity of the method, a comparatively high light intensity can be used (e.g., in the range about 1-3 mW/cm$^2$).

In order to determine if a compound is an electron acceptor, an electron donor (e.g., NADH or EDTA) can be added to the sample buffer to supply electrons to the photo-excited dye. The electron donor reduces the concentration of the dye cation radical and maintains an increased concentration of the dye anion radical. In order to test whether a compound is an electron donor, no separate electron donor is necessary. In both cases, a probe can be added (e.g., NBD-Cl or XTT) to react with superoxide and produce a detectable product. The product can be measured, for example, as an increase in absorbance at 470 nm. The difference between the probe absorbance at 470 nm in the presence of the compound to be tested and a control without the compound can be taken as a measure of redox activity of the compound.

When oxygen is unable to intercept all electrons from the dye anion radical, the dye anion radical may disproportionate and form a colorless compound. This process also may serve as a detectable variable corresponding to the redox activity of the tested compound. A compound with electron-acceptor properties intercepts electrons from dye anion radical and thus slows down the rate of dye photo-bleaching. A compound with electron-donor properties donates electrons to the dye cation radical, thus stabilizing the dye anion radical and increasing the rate of dye photo-bleaching.

Example 2

Measuring Redox Properties of Doxorubicin

Figure 2:
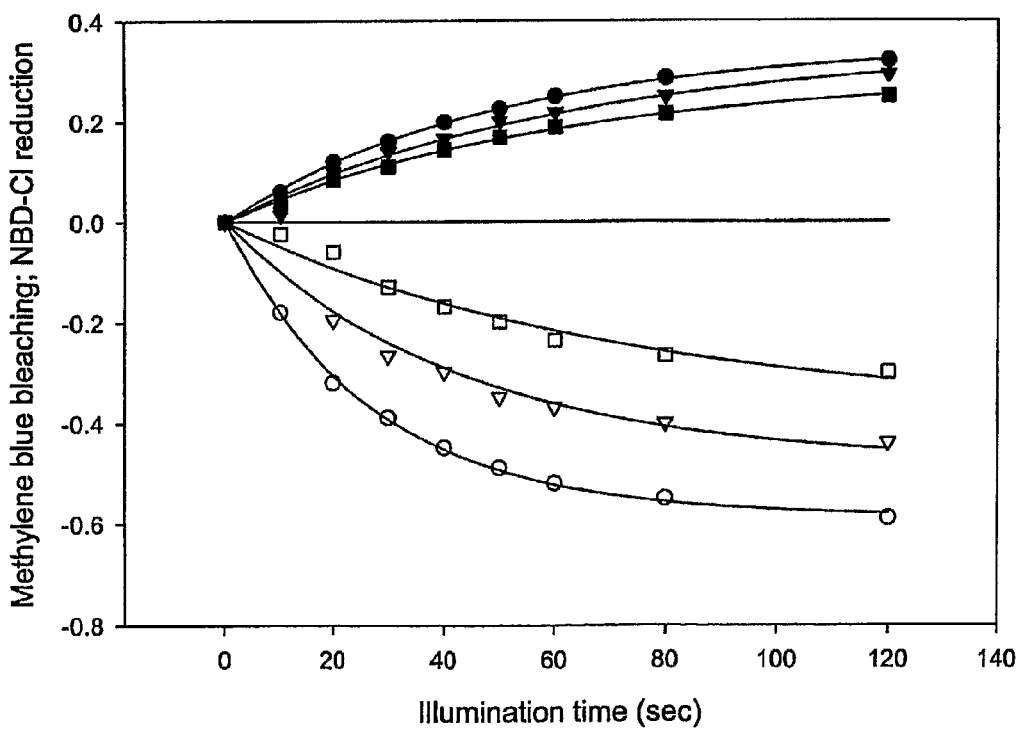
FIG. 2 is a plot of total change in absorbance versus illumination time (seconds) for evaluation of the redox activity of doxorubicin showing both increasing absorbance by NBD-Cl at 470 nm (upper portion) and decreasing absorbance by methylene blue at 663 nm (lower portion).

FIG. 2 is a plot of total change in absorbance versus illumination time for evaluation of the redox activity of doxorubicin. Doxorubicin is a potent anticancer drug, which has been shown to activate the sarcoplasmic reticulum Ca$^{2+}$ release channel, possibly, by oxidizing endogenous thiols (see reference 26). In a reaction with the photo-excited dye methylene blue, doxorubicin dose-dependently decreased the rate of photo-reduction of NBD-Cl compared to the control. The increasing absorbance at 470 nm caused by NBD-Cl reduction is shown in the upper portion (closed symbols) and the decreasing absorbance at 663 nm caused by methylene blue bleaching is shown in the lower portion (open symbols). The tested mixture included 10 µM methylene blue, 100 µM NADH and 50 µM NBD-Cl in 2 mL of a 10 mM Tris-HCl solution in water. The pH of the tested mixture was 7.4. The tested concentrations of doxorubicin were zero (○, ●), 25 µM (∇, ▼) and 50 µM (□, ■). As shown in FIG. 2, increasing the concentration of doxorubicin decreased the rates of both NBD-Cl reduction and methylene blue bleaching. Thus, FIG. 2 shows that doxorubicin is an electron acceptor.

Example 3

Measuring Redox Properties of Tetracaine and Verapamil

Figure 3:
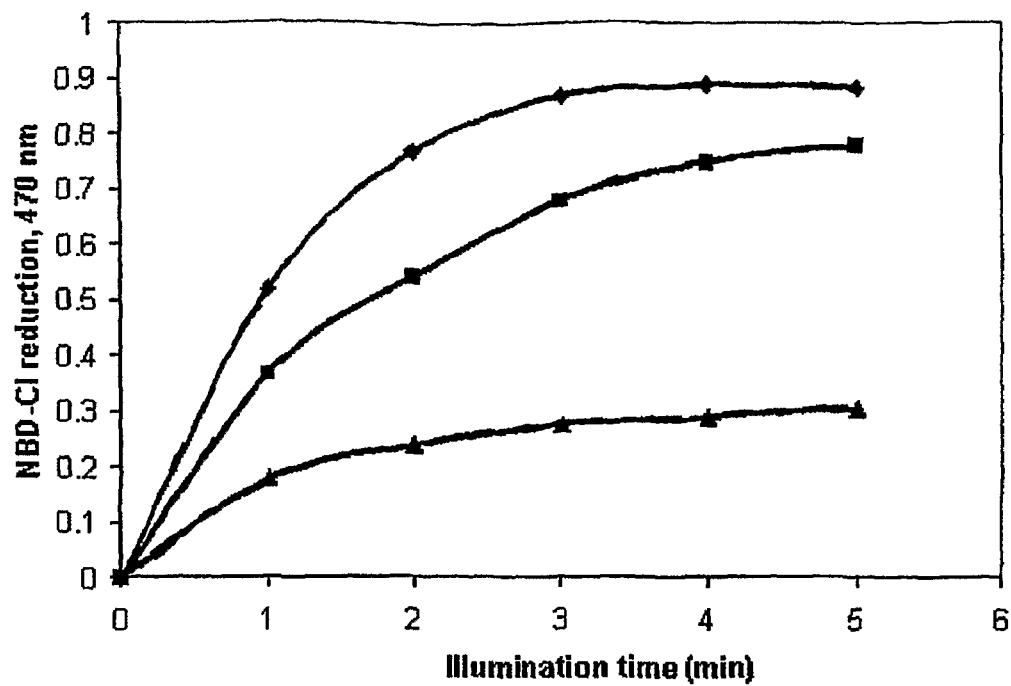
FIG. 3 is a plot of total increase in absorbance at 470 nm versus illumination time (minutes) for evaluation of the redox activity of tetracaine and verapamil.

FIG. 3 is a plot of total increase in absorbance at 470 nm versus illumination time for evaluation of the redox activity of tetracaine and verapamil. Tetracaine and verapamil are known to inhibit the sarcoplasmic reticulum Ca$^{2+}$ release channel. Tetracaine also inhibits Na$^+$ channels, while verapamil inhibits L-type Ca$^{2+}$ channels (see references 27-28). Because of the hydrophobicity of these drugs, their redox activity was assayed in the presence of an organic solvent using the dye erythrosin. The increasing absorbance at 470 nm shown in FIG. 3 is caused by NBD-Cl reduction. The tested mixture included 10 µM erythrosin and 50 µM NBD-Cl in 2 mL of a solution of 80% dimethyl sulfoxide and 20% buffer. The buffer was a 1 mM Tris-HCl solution in water. The pH of the tested mixture was 7.4. FIG. 3 shows the results of a control trial (▲), a trial with 200 μM tetracaine (■) and a trial with 200 μM verapamil (♦). As shown in FIG. 3, both tetracaine and verapamil increased the rate of NBD-Cl reduction. Thus, FIG. 3 shows that both tetracaine and verapamil are electron donors. The relative degree of electron donor activity in tetracaine and verapamil can be evaluated based on the difference in the level to which they increase the rate of NBD-Cl reduction. Based on FIG. 3, verapamil appears to be a stronger electron donor than tetracaine. Verapamil also is a more potent inhibitor of the sarcoplasmic reticulum $Ca^{2+}$ release channel than tetracaine.

Example 4

Measuring Redox Properties of Docosahexaenoic Acid

Figure 4:
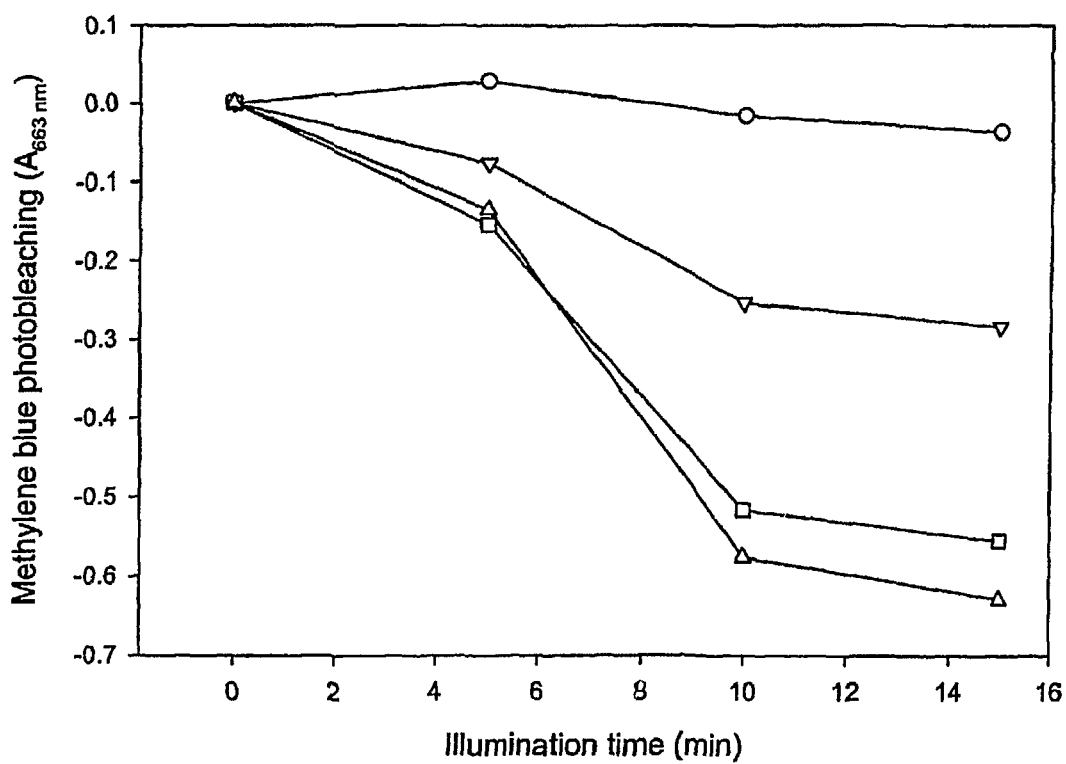
FIG. 4 is a plot of total decrease in absorbance at 633 nm versus illumination time (minutes) for evaluation of the redox activity of docosahexaenoic acid.

FIG. 4 is a plot of total decrease in absorbance at 633 nm versus illumination time for evaluation of the redox activity of docosahexaenoic acid. Docosahexaenoic acid has been shown to reduce the intensity of $Ca^{2+}$ sparks in single rat myocytes and to inhibit single-channel activity of the cardiac calcium release channel at micromolar concentrations (see reference 29). The decreasing absorbance at 633 nm shown in FIG. 4 is caused by methylene blue bleaching. The tested mixture included 10 μM methylene blue in 2 mL of a solution of 80% dimethyl sulfoxide and 20% buffer. The buffer was a 1 mM Tris-HCl solution in water. The pH of the tested mixture was 7.4. The tested concentrations of docosahexaenoic acid were zero (○), 40 μM (▽), 400 μM (□), and 800 μM (△). As shown in FIG. 4, increasing the concentration of docosahexaenoic acid increased the rate of methylene blue bleaching. Thus, FIG. 4 shows that docosahexaenoic acid is an electron donor.

Example 5

Measuring Redox Properties of Bepridil

Figure 5:
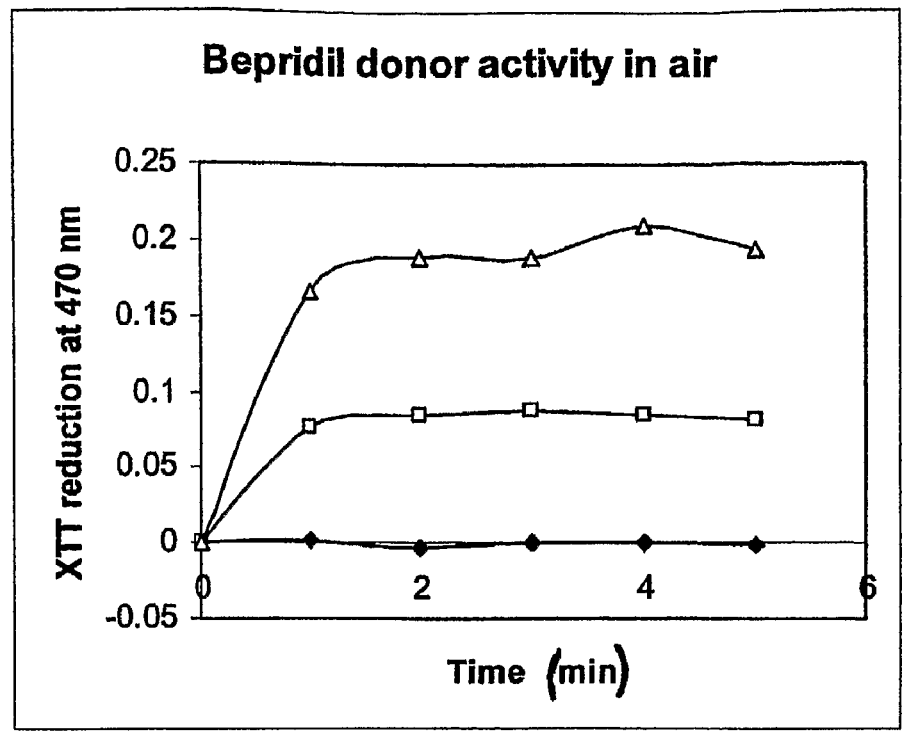
FIG. 5 is a plot of total increase in absorbance at 470 nm versus illumination time (minutes) for evaluation of the redox activity of bepridil.

FIG. 5 is a plot of total increase in absorbance at 470 nm versus illumination time for evaluation of the redox activity of bepridil. Bepridil has been shown to be cardio protective due to its activation of the mitochondrial ATP-dependent potassium channel (see reference 30). It also inhibits voltage-dependent calcium channels (see reference 31). The increasing absorbance at 470 nm shown in FIG. 5 is caused by XTT reduction. The tested mixture included 10 μM eosin and 50 μM XTT in 300 μL of 1 mM Tris-HCl solution in water. The pH of the tested mixture was 7.4. The tested concentrations of bepridil were zero (♦), 20 μM (□), and 200 μM (△). As shown in FIG. 5, increasing the concentration of bepridil increased the rate of XTT reduction. Thus, FIG. 5 shows that bepridil is an electron donor.

Example 6

Measuring Redox Properties of Diethyl Benzocaine and Ajmalin

Figure 6:
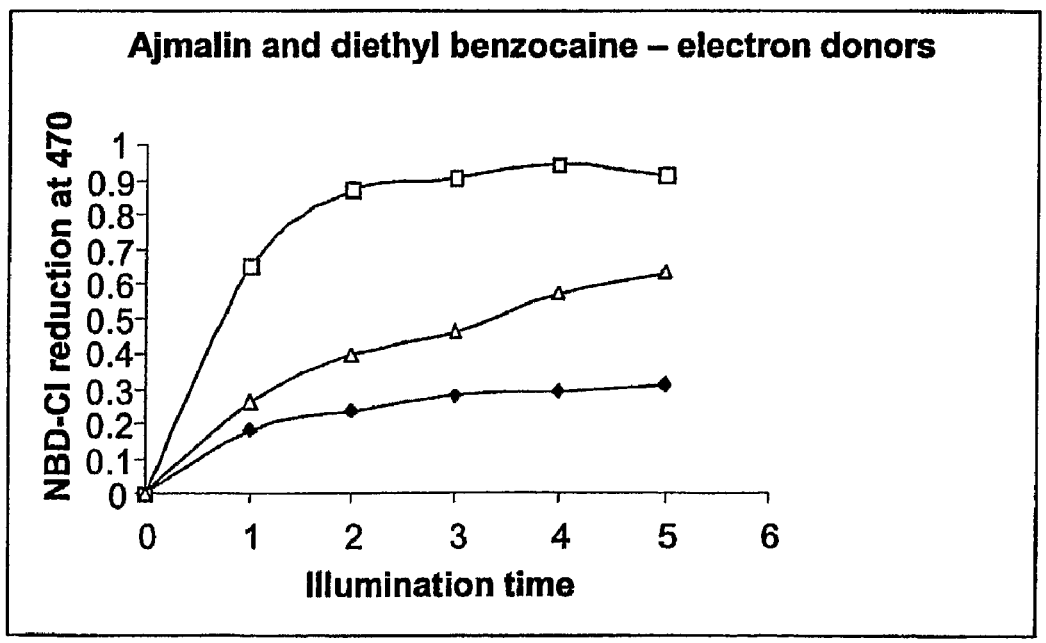
FIG. 6 is a plot of total increase in absorbance at 470 nm versus illumination time (minutes) for evaluation of the redox activity of diethyl benzocaine and ajmalin.

FIG. 6 is a plot of total increase in absorbance at 470 nm versus illumination time for evaluation of the redox activity of diethyl benzocaine and ajmalin. Diethyl benzocaine and ajmalin have been shown to block Na+ channels (see references 32-33). Diethyl benzocaine has also been shown to activate the mitochondrial ATP-dependent potassium channel (see reference 3). The increasing absorbance at 470 nm shown in FIG. 6 is caused by NBD-Cl reduction. The tested mixture included 10 μM erythrosin and 50 μM NBD-Cl in 2 mL of a solution of 80% dimethyl sulfoxide and 20% buffer. The buffer was a 1 mM Tris-HCl solution in water. The pH of the tested mixture was 7.4. FIG. 6 shows the results of a control trial (♦), a trial with 2 mM diethyl benzocaine (△) and a trial with 200 μM ajmalin (□). As shown in FIG. 6, both diethyl benzocaine and ajmalin increased the rate of NBD-Cl reduction. Thus, FIG. 6 shows that both diethyl benzocaine and ajmalin are electron donors. The relative degree of electron donor activity in diethyl benzocaine and ajmalin can be evaluated based on the difference in the level to which they increase the rate of NBD-Cl reduction. Based on FIG. 6, ajmalin appears to be a stronger electron donor than diethyl benzocaine.

Example 7

Measuring Redox Properties of Ryanodine

Figure 7:
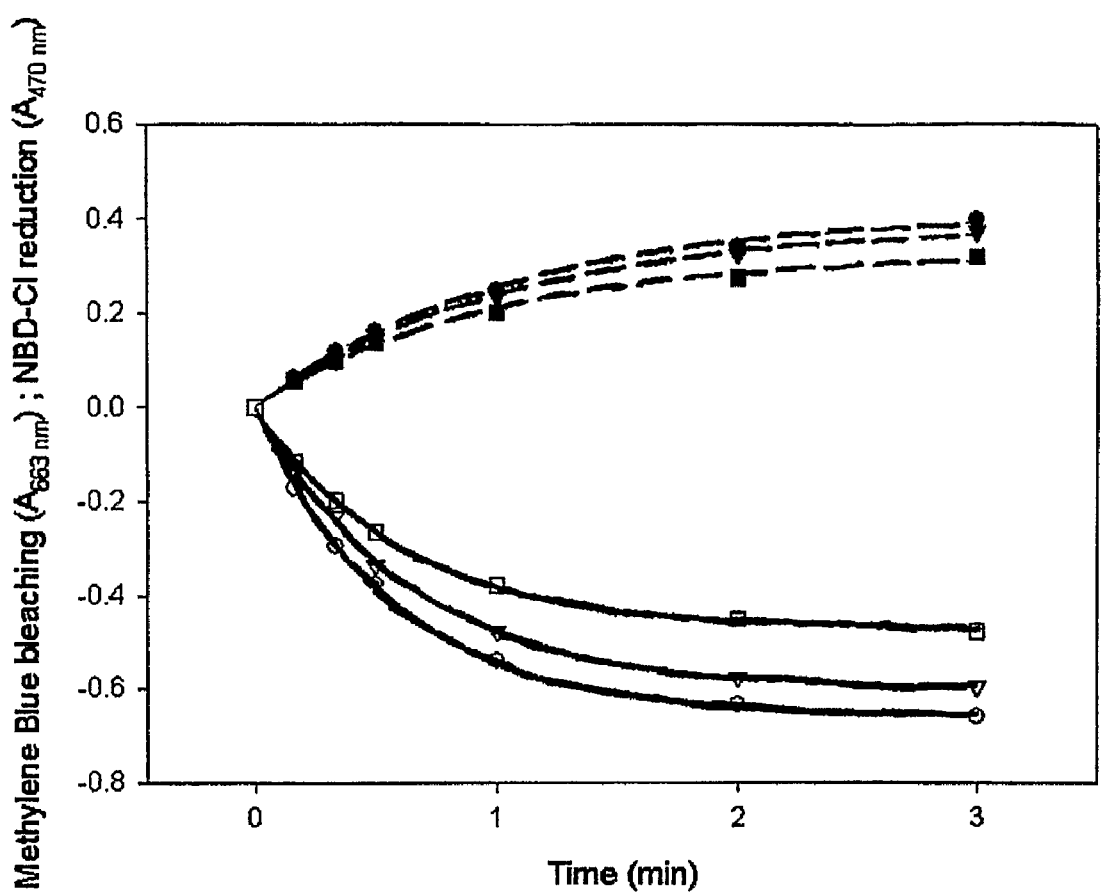
FIG. 7 is a plot of total change in absorbance versus illumination time (minutes) for evaluation of the redox activity of ryanodine showing both increasing absorbance at 470 nm (upper portion) and decreasing absorbance at 663 nm (lower portion).

FIG. 7 is a plot of total change in absorbance versus illumination time for evaluation of the redox activity of ryanodine. Ryanodine is a specific activator of the calcium release channel at concentrations of 1-2 □M. The increasing absorbance at 470 nm caused by NBD-Cl reduction is shown in the upper portion (closed symbols) and decreasing absorbance at 663 nm caused by methylene blue bleaching measured at 663 nm is shown in the lower portion (open symbols). The tested mixture included 10 μM methylene blue, 100 μM NADH and 50 μM NBD-Cl in 2 mL of a solution of 80% dimethyl sulfoxide and 20% buffer. The buffer was a 1 mM Tris-HCl solution in water. The pH of the tested mixture was 7.4. The tested concentrations of ryanodine were zero (○, ●), 1 μM (▽, ▼), and 2 μM (□, ■). As shown in FIG. 7, increasing the concentration of ryanodine decreased the rates of both NBD-Cl reduction and methylene blue bleaching. Thus, FIG. 7 shows that ryanodine is an electron acceptor.

Example 8

NBD-Cl for Monitoring Superoxide Concentration

This example demonstrates that NBD-Cl can be used to rapidly detect and quantify superoxide production generated by several different processes. Specifically, highly-sensitive spectrophotometric methods were used to measure the concentration of superoxide derived from $KO_2$, generated by the xanthine-xanthine oxidase reaction, and generated by the addition of NADH to skeletal muscle sarcoplasmic reticulum vesicles. The spectrophotometric methods involved the reaction of superoxide with NBD-Cl. The concentration of the product of this reaction was monitored either by recording absorbance at a wavelength of 470 nm or by measuring the fluorescence emission intensity at 550 nm using an excitation wavelength of 470 nm. The extinction coefficient of the active product was determined to be 4000 $M^{-1}cm^{-1}$. A lower limit second-order bimolecular rate constant of $1.5\pm0.3\times10^5$ $M^{-1}s^{-1}$ was estimated from kinetic stopped-flow analysis for the reaction between NBD-Cl and $KO_2$. A plot of absorbance versus concentration of superoxide was linear over the range 2-200 μM $KO_2$ while higher sensitivities were obtained from fluorometric measurements down into sub-micromolar concentrations with a limit of detection of 100 nM $KO_2$.

This technique showed higher specificity when compared to some other commonly used methods for detection of superoxide (i.e. nitroblue tetrazolium). The results presented showed good experimental agreements with rates obtained for the measurement of superoxide when compared to other well known probes such as acetylated ferri cytochrome-C and XTT.

Both a Lambda 25 Perkin-Elmer double beam and a HP 8452 spectrophotometer were used in the spectrophotometric measurements described in this example. Rate of formation and absorbance measurements in the reaction between NBD-Cl and $KO_2$ in DMSO were obtained using a Hi-Tech SF-61 DX2 double-mixing stopped-flow spectrophotometer. Fluorometric measurements were carried using a Spex Fluorolog 0.22 m double spectrometer using slit widths of 2.5 mm and 1.25 mm for the excitation and emission wavelengths respectively. Characterization of the product was carried out by setting the excitation wavelength at 470 nm and emission scans were performed between wavelength ranges of 480 nm and 680 nm.

NBD-Cl was purchased from Fluka and Riedel-de Haën (Switzerland). Ten millimolar stock solutions of NBD-Cl were prepared using acetonitrile as a solvent. The stock solution was stable in the dark for several days. Potassium superoxide ($KO_2$) was purchased from Sigma-Aldrich (St. Louis, Mo.) and 10 mM solutions were prepared daily by dissolving a weighed amount in DMSO and then vigorously stirring for about 15 minutes. All spectrophotometric measurements were carried out either in DMSO or phosphate buffer (50 mM $KH_2PO_4$ and 10 mM KCl) adjusted to pH 7.4. Xanthine solution was made fresh by dissolving xanthine in a minimal volume of 1 M KOH. This was followed by dilution with deionized water and adjusting the pH to 7.4 with 1 M HCl. Xanthine oxidase solution was prepared immediately before use in phosphate buffer. SR vesicles were isolated from rabbit fast twitch skeletal muscle (see reference 34). All buffers used in the isolation of the SR included 50 µM dithiothreitol and 0.2 µg/ml leupeptin, except for the final SR resuspension buffer.

Figure 8:
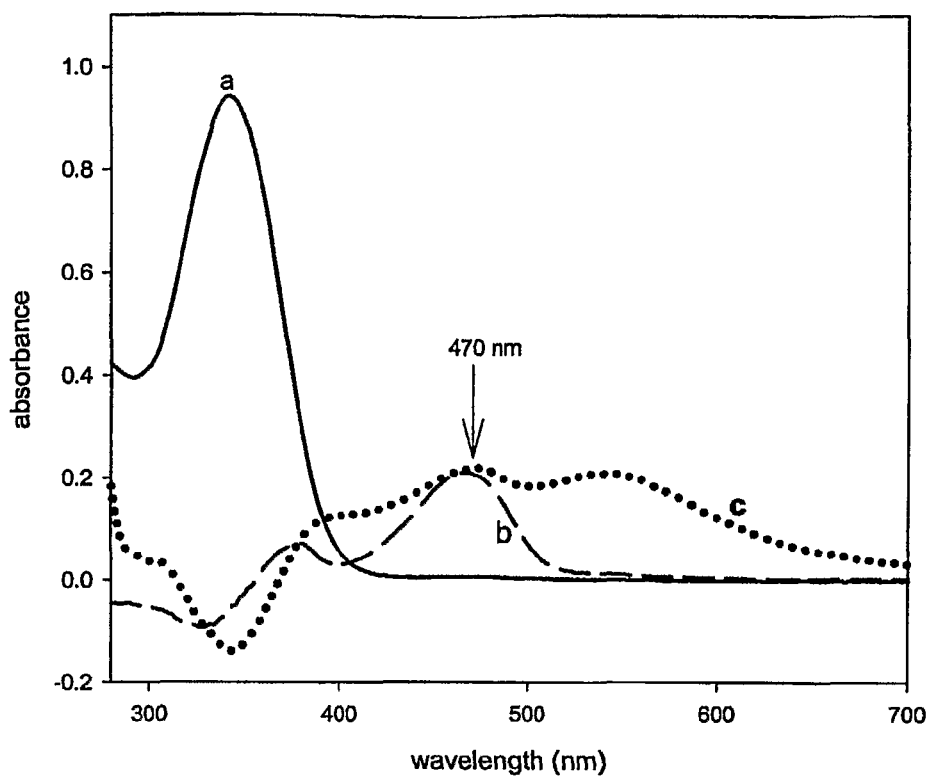
FIG. 8 is a plot of absorption spectra generated from NBD-Cl in the presence and absence of superoxide.

FIG. 8 is a plot of absorption spectra generated from NBD-Cl in the presence and absence of superoxide. Trace "a" shows the results of testing 100 µM NBD-Cl in DMSO. Trace "b" shows the results of testing 200 µM NBD-Cl and 40 µM $KO_2$ in DMSO. Trace "c" shows the results of testing 0.1 mg/ml SR, 100 µM NBD-Cl and 40 µM NADH in phosphate buffer at pH=7.4.

Figure 9:
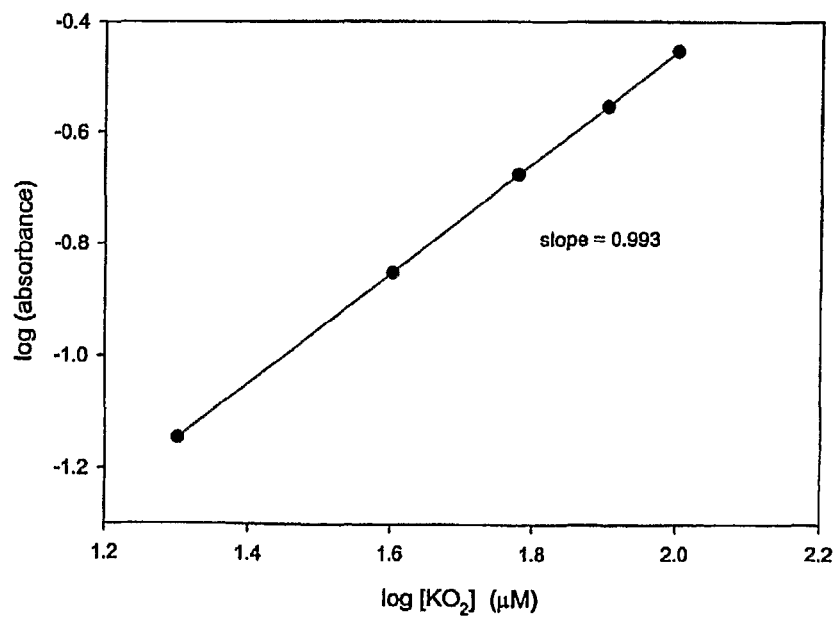
FIG. 9 is a logarithmic plot for the reaction of different concentrations of $KO_2$ with a fixed NBD-Cl concentration.

As shown by trace "a" in FIG. 8, NBD-Cl has a characteristic absorption peak at 343 nm. The reaction between NBD-Cl and $KO_2$, both in DMSO and in phosphate buffer, produced a stable reaction product with a characteristic absorbance peak at 470 nm, as shown in trace "b" of FIG. 8. Trace "b" is a difference spectrum obtained by subtracting absorbance spectrum of NBD-Cl from its new spectrum following reaction with $KO_2$. FIG. 9 is a log-log plot of the absorbance at 470 nm as function of $KO_2$ concentration. The calculated extinction coefficient from the measured absorbance was 4000±137 $M^{-1}cm^{-1}$. The formation of the reaction product was extremely fast (proceeding to completion in less than 1 second) with a second order rate constant of $1.5\pm0.3\times10^5$ $M^{-1}s^{-1}$ recorded on a Hi-Tech SF-61 DX2 stopped-flow spectrophotometer (data not shown).

Trace "c" in FIG. 8, which was generated when NBD-Cl was used in the quantification of superoxide in the presence of biological proteins, includes a second absorption peak at 540 nm. The presence of this peak was not found to enhance the absorbance measured at 470 nm. Additional experiments carried out (data not shown) revealed the existence of an isosbestic point at around 485 nm. This allows the absorbance at 470 nm to remain constant even when absorbance at 540 nm fluctuates due to modification in the protein environment. This conclusion is further substantiated by the fact that NBD-Cl assays at 470 nm from 40 µM $KO_2$ in DMSO gave the same absorption value as the assays with 40 µM NADH in the presence of SR (see reference 42).

Figure 10:
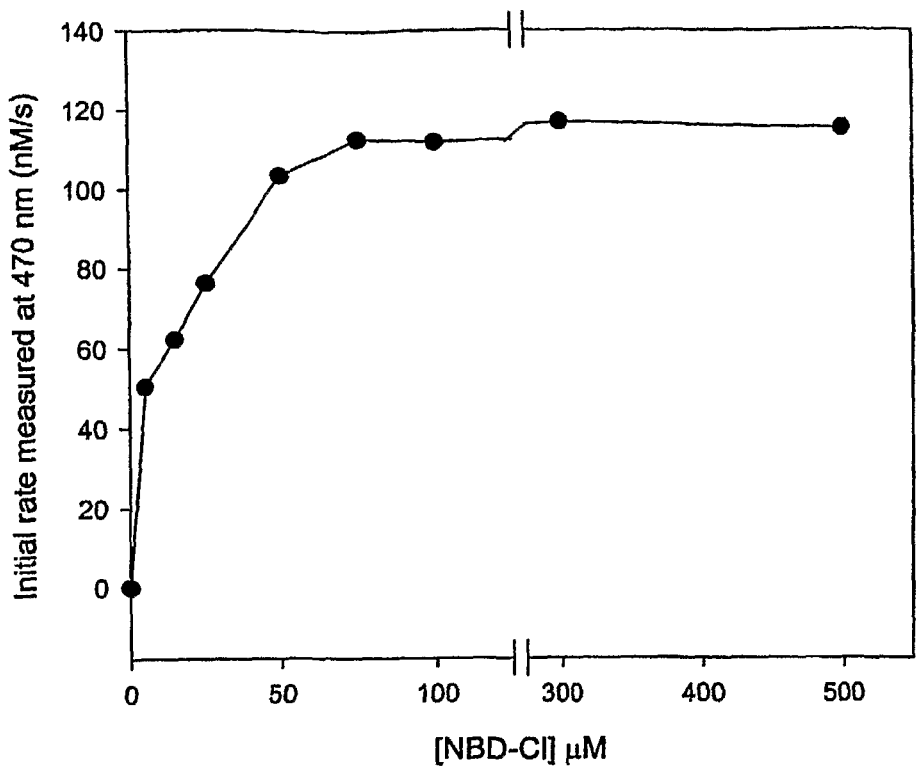
FIG. 10 is a plot of initial rate measured at 470 nm versus concentration of NBD-Cl.

The sensitivity of NBD-Cl for the detection of superoxide was optimized by using fixed concentrations of xanthine and xanthine oxidase (see references 35-36) and varying concentrations of NBD-Cl until an upper limiting rate of reduction was reached. The xanthine-xanthine oxidase reaction affords slow generation of superoxide, which allows for efficient detection by NBD-Cl despite the spontaneous dismutation of superoxide to peroxide that occurs in an aqueous environment. The results are shown in FIG. 10. The concentrations of xanthine and xanthine oxidase were fixed at 50 µM and 50 nM, respectively, while the concentration of NBD-Cl was varied from 0 to 500 µM. The extinction coefficient at 470 nm was 4000 $M^{-1}$ $cm^{-1}$. All measurements were carried out in phosphate buffer at pH 7.4. FIG. 10 reveals that a concentration of 100 µM NBD-Cl is optimum for the measurement of superoxide generated over a given period. Further increases in the initial concentration of NBD-Cl did not produce any further change in the maximum initial rates at the corresponding absorption wavelength of 470 nm.

Figure 11:
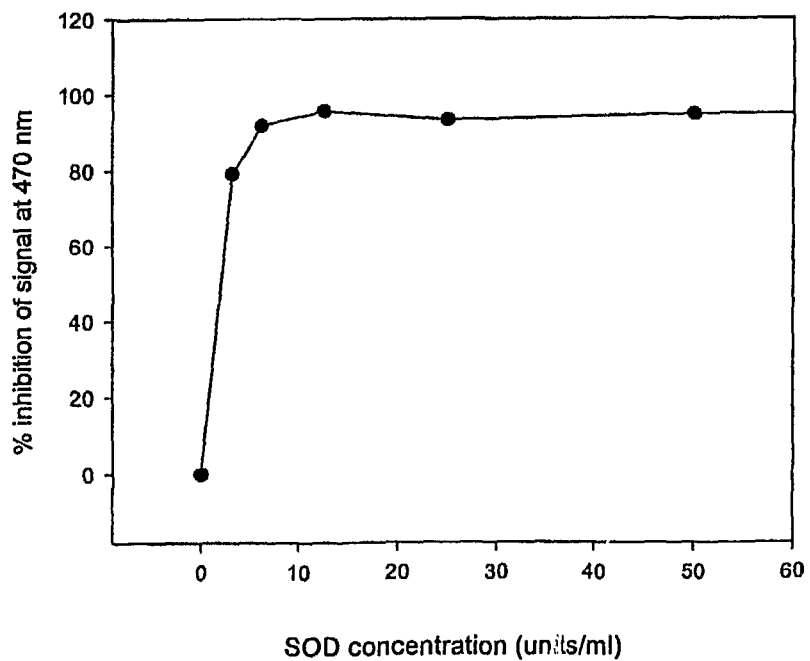
FIG. 11 is a plot of % inhibition of signal at 470 nm versus superoxide dismutase concentration.

The role of superoxide in the NBD-Cl reaction is demonstrated in FIG. 11, which shows inhibition of the 470 nm signal associated with varying concentrations of SOD. The concentrations of xanthine, xanthine oxidase and NBD-Cl were 50 µM, 150 nM and 100 µM, respectively. All measurements were carried out in phosphate buffer at pH=7.4. FIG. 11 shows that SOD concentrations greater than 10 units/mL were sufficient for complete elimination of the signal at 470 nm.

Figure 12A:
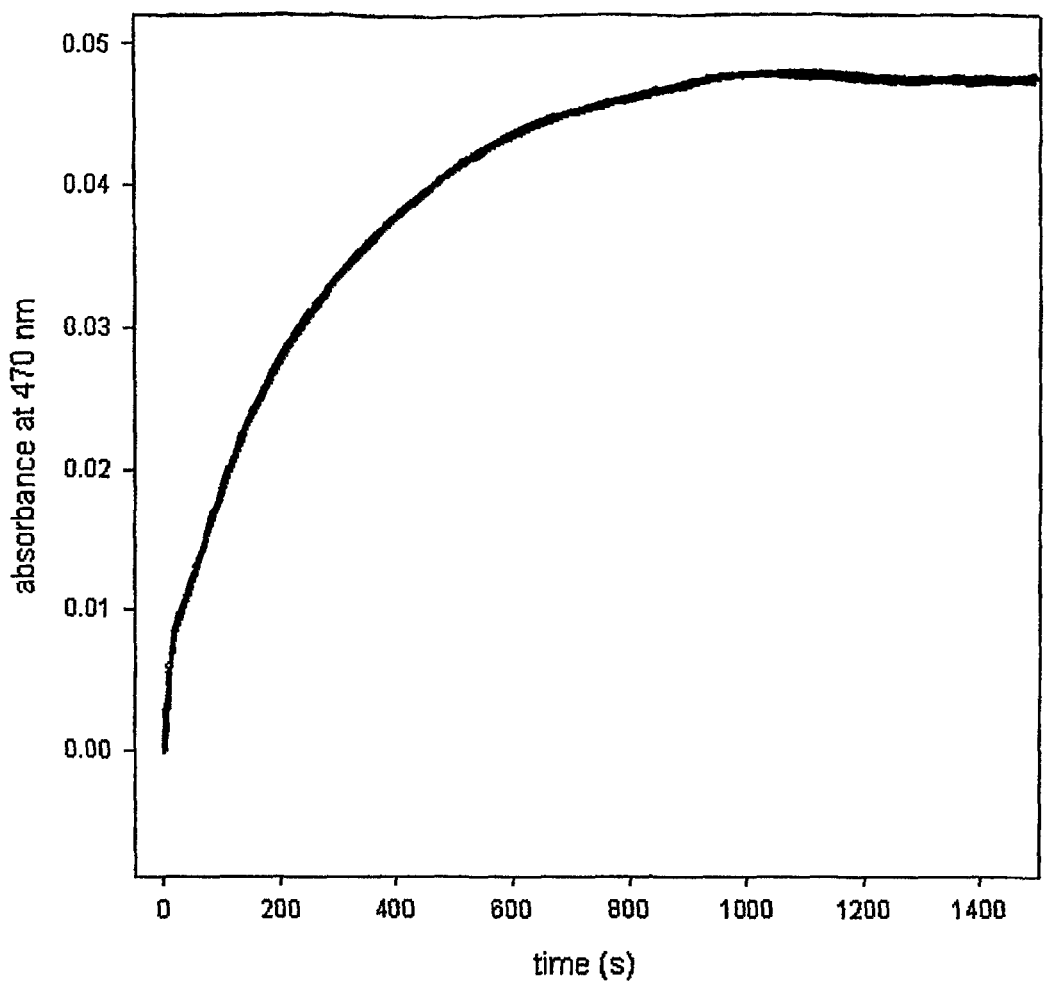
FIG. 12A is a time-dependent profile for NBD-Cl reaction with superoxide at 470 nm in the xanthine-xanthine oxidase reaction.
Figure 12B:
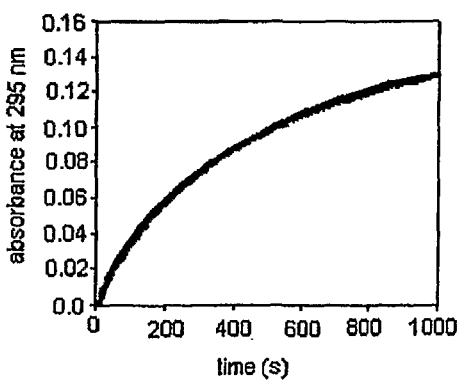
FIG. 12B shows time-dependent profile for uric acid formation at 295 nm measured under identical conditions in the absence of NBD-Cl.
Figure 12C:
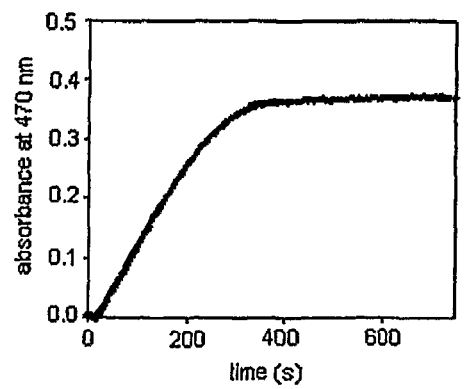
FIG. 12C shows xanthine-xanthine oxidase reaction followed at 470 nm under the same concentrations described above but using 600 µM 2,3-bis(2-methoxy-4-nitro-5-sulphophenyl)-5-[(phenylamino)carbonyl]-2H-tetrazolium hydroxide as the probe.

FIG. 12A shows a typical time dependent absorbance trace obtained at 470 nm using NBD-Cl as a probe upon addition of 15 µM xanthine and 100 nM xanthine oxidase. The maximum absorbance of 0.048 corresponds to a measured amount of superoxide equal to 12.0 µM. Xanthine oxidase converts one mole of xanthine and $O_2$ to one mole of uric acid with the generation of superoxide. Using the extinction coefficient $\epsilon_{470}=4000 M^{-1}cm^{-1}$, superoxide generated was quantified by NBD-Cl. FIG. 12B shows the absorbance-time profile obtained when production of uric acid was monitored at 295 nm from the xanthine-xanthine oxidase reaction in the absence of any superoxide probe. This reaction profile suggests that addition of NBD-Cl has a slight activating effect on the reaction dynamics leading to the formation of uric acid based on comparison of time required to completely react with all of the xanthine present. In contrast, replacement of NBD-Cl with 600 µM XTT as a superoxide probe, as shown in FIG. 12C, causes about a two-fold increase in the rate of superoxide formation. Thus, XTT significantly activates the enzymatic production of superoxide during the xanthine-xanthine oxidase reaction.

Table 1 shows the results of a comparative study involving measurement of initial rates of superoxide formation in the xanthine-xanthine oxidase reaction using NBD-Cl, XTT and cytochrome C (acetylated) as superoxide probes. The tested concentrations of NBD-Cl, NBT, cytochrome C and XTT were 100 µM, 100 µM, 80 g/ml and 600 µM, respectively. The concentrations of xanthine and xanthine oxidase were 50 µM and 150 nM, respectively. The extinction coefficients ($mM^{-1}$ $cm^{-1}$) for NBD-Cl, NBT, cytochrome C and XTT were 4.0, 15.0, 16.8 and 21.6, respectively, at their indicated wavelengths. All measurements were made in phosphate buffer at pH 7.4. Table 1 shows that there is closer agreement in measurements obtained for NBD-Cl and cytochrome C than for XTT and NBT. As mentioned above, NBT may have specificity problems.

TABLE 1

| Xan./Xan. Ox. Reaction | Superoxide at 470 nm | Superoxide at 550-540 nm | Superoxide at 550 nm |
|---|---|---|---|
| +NBD-Cl | 0.127 ± 0.002 | — | — |
| +Cytochrome C (acetylated) | — | 0.101 ± 0.007 | — |
| +NBT | — | — | 0.038 ± 0.002 |
| +XTT | 0.225 ± 0.010 | — | — |

Figure 13:
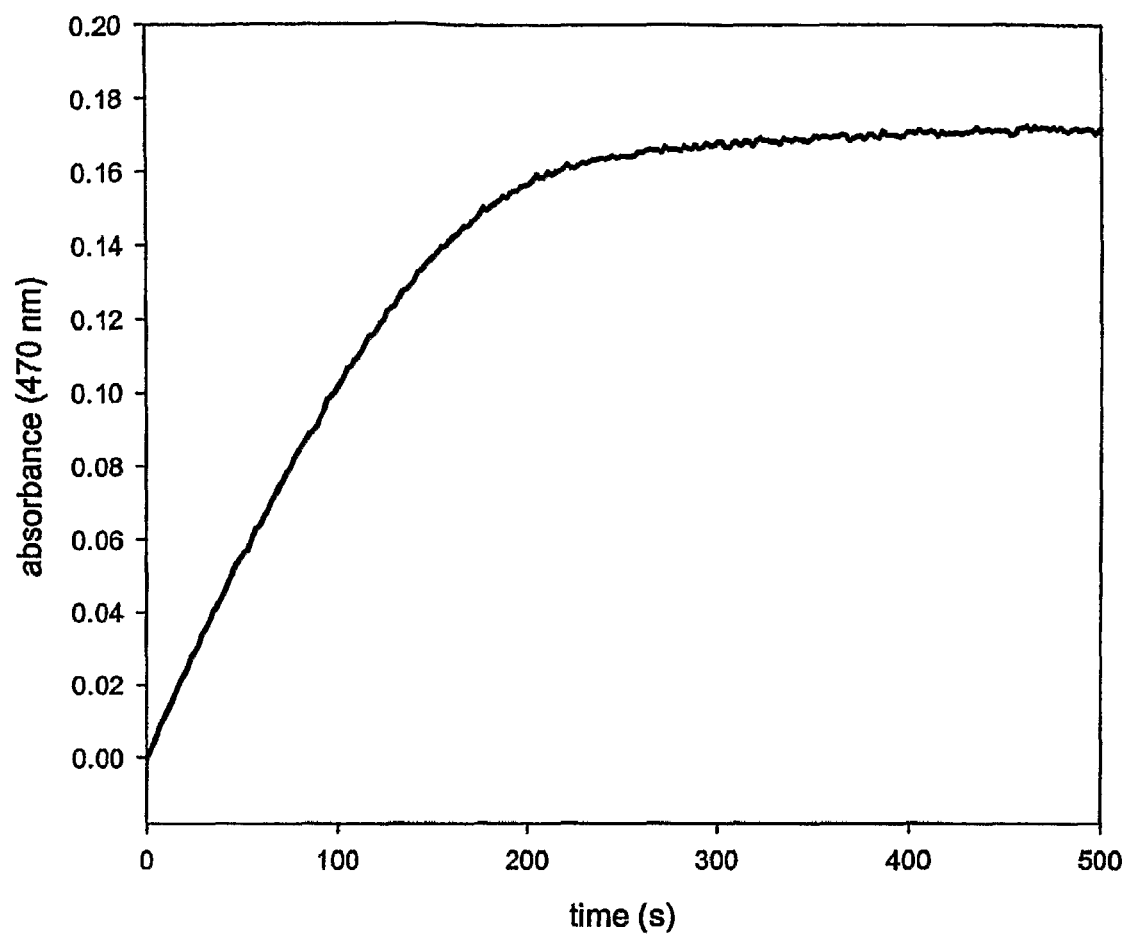
FIG. 13 is a typical reaction profile with NBD-Cl used as a probe for measuring superoxide generated with sarcoplasmic reticulum (SR) vesicles and NADH.

In another trial, generation of superoxide by SR and NADH (see reference 24) was assayed using XTT, cytochrome C and NBD-Cl by following absorbance for both XTT and NBD-Cl at 470 nm and for cytochrome C at 550 nm. Using extinction coefficients ($mM^{-1}cm^{-1}$) of 21.6 for XTT (see reference 37), 4.0 for NBD-Cl and 21.0 for cytochrome C (see reference 14), the measured superoxide concentrations were 33.1, 38.5 and 26.3 respectively, after initiating each reaction with 40 μM of NADH. The concentration of SR was 0.1 mg/mL, the concentration of NBD-Cl was 100 μM and the concentration of NADH was 40 μM. Measurement was carried out in phosphate buffer at pH 7.4. As illustrated in FIG. 13, NBD-Cl was similar to XTT and cytochrome C as far as its ability to measure comparable amounts of superoxide. In the presence of superoxide dismutase, detection of superoxide by NBD-Cl was completely inhibited, showing that superoxide was responsible for the peak at 470 nm.

Figure 14:
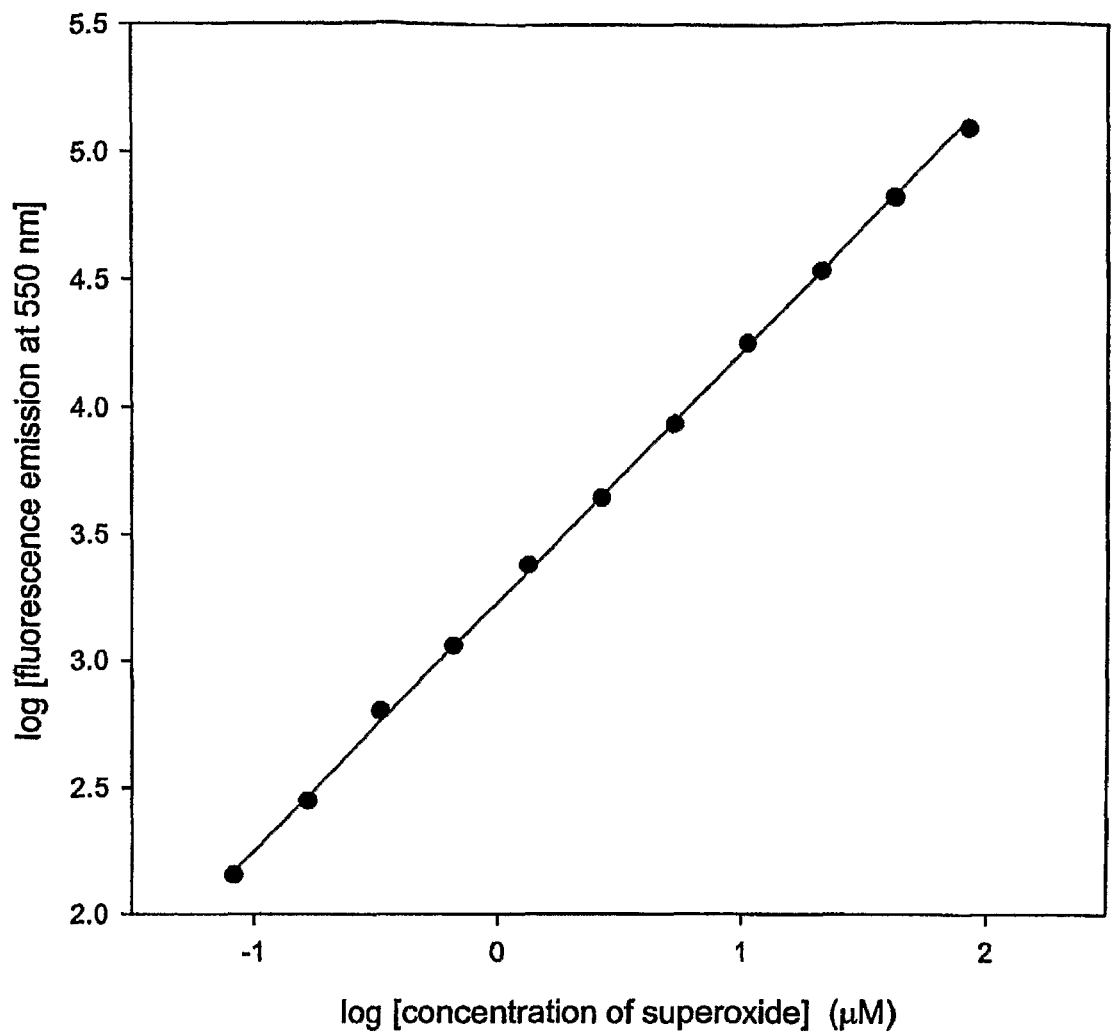
FIG. 14 is a calibration curve for the measurement of superoxide concentration from fluorescence emission of the NBD-Cl product.

The product of the reaction between NBD-Cl and $KO_2$ has been shown to have a characteristic absorbance at 470 nm in an aqueous environment. However, upon excitation at 470 nm (slit width 2.5 mm) in a fluorimeter, an emission was not observed except when organic solvent was present in the medium. Results show that by reducing the polarity of the reaction medium, the fluorescent intensity of the signal can be increased. Optimization of the fluorescence signal involved first generating a calibration curve from varying concentrations of the NBD-Cl product in an aqueous medium. After mixing 1 mL of this NBD-Cl product solution with 2 mL of organic solvent, the fluorescence signal was read at the emission peak of 550 nm (slit width 1.25 mm). The solvent used for activating NBD-Cl product fluorescence was acetonitrile. The calibration curve was derived by plotting the fluorescence intensity at 550 nm as a function of the starting concentration of NBD-Cl product. Quantification of superoxide generated from other sources such as from xanthine-xanthine oxidase reaction and phenazine methosulfate-NADH reactions were measured by following the protocol described above. A typical calibration obtained is shown in FIG. 14 using 100 μM of NBD-Cl and different concentrations of $KO_2$. A plot of log of fluorescence versus log of superoxide concentration was linear in the range of 0.1 μM to 100 μM.

The results presented in this example demonstrate that NBD-Cl is a good tool for measuring superoxide under conditions in which non-specific reactions of NBD-Cl are minimized. It is important to note that NBD-Cl also reacts with amines and thiols, although some of these reactions can be reduced or eliminated by controlling the pH of the environment. Previous work has found that NBD-Cl will react with thiols and sulfenic acid, forming two adducts with different absorption properties in the UV-vis region (see reference 38). The RS-NBD adduct absorbs at about 420 nm while RSO-NBD absorbs at about 350 nm (see reference 39). Tyrosyl and amine groups react with NBD-Cl favorably in alkaline pH where the absorption maxima then shift to 385 nm and 480 nm respectively (see reference 40).

Another important feature of NBD-Cl is the large rate constant obtained between NBD-Cl and superoxide ($1.5\pm0.3\times10^5$ $M^{-1}s^{-1}$) during kinetic stopped-flow measurements, suggesting that NBD-Cl can rapidly assay superoxide without significant interference from other non-specific reactions that may occur at much slower time scales. The measured second-order rate constants ($M^{-1}s^{-1}$) for cytochrome C and XTT reductions by superoxide are $4.82\pm0.73\times10^5$ and $8.59\pm0.81\times10^4$, respectively, were in good agreement with data in FIGS. 12-14 showing that NBD-Cl is as good or perhaps a better scavenger of superoxide than comparable probes. A concentration of 100 μM NBD-Cl produces sufficiently low absorbance across the UV-vis region to allow monitoring other species of interest, especially in the regions between 250 and 500 nm. XTT is well suited for quantitative measurements of superoxide at wavelengths greater than 450 nm when working at the recommended concentration of 500 to 750 μM (see reference 41). However, due to its large absorbance in the lower UV-vis region, simultaneous measurements in the UV region of the spectra are difficult (i.e. such as monitoring oxidation of NADH at 340 nm). In addition, fluorometric measurements allow lower concentrations of superoxide to be detected with greater accuracy.

Optimization of the fluorescence signal can be achieved by using an organic solvent that yields a stable fluorescence signal. The higher the slope of the calibration curve, the lower the limit of detection of superoxide. Additional experiments (data not shown) confirmed that the presence of biological species such as $H_2O_2$, NADH, NADPH and $NAD^+$ does not interfere with NBD-Cl reactions including the reactions related to quantifying superoxide in solution. However, control experiments can be performed when working in biological environments where NBD-Cl can readily react with a variety of compounds. In the presence of NBD-Cl, addition of NADH to sarcoplasmic reticulum vesicles (SR) showed superoxide formation at 470 nm that was completely inhibited by addition of SOD under aerobic conditions. At low a oxygen concentration (i.e., about 130 ppm), SR reduced NBD-Cl at rates comparable to that measured under aerobic conditions. This observation suggests that in the absence of molecular oxygen, SR passes electrons directly to NBD-Cl with little or no change in the rate of reduction of NBD-Cl. However, in the absence NBD-Cl, rates of oxidation of NADH by SR showed direct dependence on oxygen concentration. The ability of NBD-Cl to be reduced by species other than superoxide with formation of a peak at 470 nm was confirmed using the short-chain sugars, glycolaldehyde (GLA) and DL-glyceraldehyde (GA) at a concentration of 50 mM. Under aerobic conditions, the reduction of NBD-Cl was observed by these sugars, while the addition of SOD at 100 units/mL produced 50% and 66% inhibition of the 470 nm peak, respectively. Similar results were found with XTT. XTT was reduced by short-chain sugars (GLA and GA) in the presence and absence of molecular oxygen (see reference 15).

Additional information regarding the use of NBD-Cl to detect superoxide can be found in reference 42, below.

Closing

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

REFERENCE LIST

1.) Marinov, B. S. and Saxon, M. E., "Dihydropyridine $Ca^{2+}$ Agonists and Channel Blockers Interact in Opposite Manner with Photogenerated Unpaired Electrons." FEBS LETT. 186(2): 251-254 (1985).

2.) Marinov, B. S., "$Na^+$-Channel Antagonists Act as Electron Donors While Agonists Act as Electron Acceptors in Reaction with Dye Free Radicals." FEBS LETT. 191(1): 159-162 (1985).

3.) Grigoriev, S. M., ET AL., "Regulation of Mitochondrial KATP Channel by Redox Agents." BIOCHIM. BIOPHYS ACTA 1410(1): 91-96 (1999).

4.) Marinov, B. S., "Norepinephrine with its Precursors and their Antagonists Haloperidol and Phentolamine Interact with Dye Free Radicals in Opposite Ways." FEBS LETT. 198(1): 130-134 (1986).

5.) Marinov, B. S. and Ruzieva, R. K., "Opposite Control of Oxygen Affinity for Hemoglobin by Electron Donors and Acceptors." BIOKHIMIIA 55(9): 1616-1623 (1990).

6.) Marinov, B. S. and Evtodienko, J. V, "Estimation of Redox Properties of Chemical Compounds by Their Reactions with Free Radicals." ANAL. BIOCHEM. 220(1): 154-159 (1994).

7.) Dambrova, M., ET AL., "Improved Method for EPR Detection of DEPMPO-Superoxide Radicals by Liquid Nitrogen Freezing." BIOCHEM. BIOPHYS. RES. COMMUN. 275(3): 895-898 (2000).

8.) Vasquez-Vivar, J., ET AL., "Mitochondrial Aconitase is a Source of Hydroxyl Radical. An Electron Spin Resonance Investigation." J. BIOL. CHEM. 275(19): 14064-14069 (2000).

9.) Valgimigli, M., ET AL., "Oxidative Stress EPR Measurement in Human Liver by Radical-Probe Technique. Correlation with Etiology, Histology and Cell Proliferation." FREE RADIC. RES. 36(9): 939-948 (2002).

10.) Kelm, M., ET AL., "The Nitric Oxide/Superoxide Assay. Insights into the Biological Chemistry of the NO/O-2. Interaction." J. BIOL. CHEM. 272(15): 9922-9932 (1997).

11.) Nagano, S., ET AL., "Flow Cytometric Measurement of NBT-Reducing Activity in Peripheral Leukocytes Applying THMS H.1™." RINSHO BYORI. 38(7): 794-798 (1990).

12.) Cassina, A. M., ET AL., "Cytochrome C Nitration by Peroxynitrite." J. BIOL. CHEM. 275(28): 21409-21415 (2000).

13.) Thomson, L., ET AL., "Kinetics of Cytochrome C2+ Oxidation by Peroxynitrite: Implications for Superoxide Measurements in Nitric Oxide-Producing Biological Systems." ARCH. BIOCHEM. BIOPHYS. 319(2): 491-497 (1995).

14.) Tarpey, M. M. and Fridovich, I., "Methods of Detection of Vascular Reactive Species Nitric Oxide, Superoxide, Hydrogen Peroxide, and Peroxynitrite." CIRC. RES. 89(3): 224-236 (2001).

15.) Benov, L. and Fridovich, I., "Is Reduction of the Sulfonated Tetrazolium 2,3-bis(2-methoxy-4-nitro-5-sulfophenyl)-2-tetrazolium-5-carboxanilide a Reliable Measure of Intracellular Superoxide Production?" ANAL. BIOCHEM. 310 (2): 186-190 (2002).

16.) Price, N. C., ET AL., "Fluorescent and Spin Label Probes of the Environments of the Sulfhydryl Groups of Porcine Muscle Adenylate Kinase." J. BIOL. CHEM. 250(2): 644-652 (1975).

17.) Lopina, O. D., ET AL., "Investigation of Sarcoplasmic Reticulum SH-Groups." BIOKHIMIIA. 44(2): 306-316 (1979).

18.) Stuchbury, T., ET AL., "A Reporter Group Delivery System with Both Absolute and Selective Specificity for Thiol Groups and an Improved Fluorescent Probe Containing the 7-nitrobenzo-2-oxa-1,3-diazole Moiety." BIOCHEM. J. 151 (2): 417-432 (1975).

19.) Becker, R., "Fluorometric Determination of Glibornuride in Plasma and Serum Using 7-chloro-4-nitrobenzo-2-oxa-1,3-diazole." ARZNEIMITTELFORSCHUNG 27(1): 102-105 (1977).

20.) Taha, E. A., "Kinetic Spectrophotometric Methods for the Determination of Dothiepin Hydrochloride in Bulk and in Drug Formulation." ANAL. BIOANAL. CHEM. 376(7): 1131-1136 (2003).

21.) El Emam, A. A., ET AL., "Determination of Lisinopril in Dosage Forms and Spiked Human Plasma Through Derivatization with 7-chloro-4-nitrobenzo-2-oxa-1,3-diazole (NBD-Cl) Followed by Spectrophotometry or HPLC with Fluorimetric Detection." J. PHARM. BIOMED. ANAL. 34(1): 35-44 (2004).

22.) Staniek, K. and Nohl, H., "$H(2)O(2)$ Detection from Intact Mitochondria as a Measure for One-Electron Reduction of Dioxygen Requires a Non-Invasive Assay System." BIOCHIM. BIOPHYS. ACTA 1413(2): 70-80 (1999).

23.) Valgimigli, L., ET AL., "Measurement of Oxidative Stress in Human Liver by EPR Spin-Probe Technique." FREE RADIC. RES. 33(2): 167-178 (2000).

24.) Xia, R., ET AL., "Skeletal Muscle Sarcoplasmic Reticulum Contains a NADH-Dependent Oxidase that Generates Superoxide." AM. J. PHYSIOL CELL PHYSIOL 285(1): C215-C221 (2003).

25.) Golfetti, R., ET AL., "Chronically Administered Acetaminophen and the Ischemia/Reperfused Myocardium." EXP. BIOL. MED. (Maywood.) 228(6): 674-682 (2003).

26.) Abramson, J. J., ET AL., "Mechanism of Anthraquinone-Induced Calcium Release from Skeletal Muscle Sarcoplasmic Reticulum." J. BIOL. CHEM. 263(35): 18750-18758 (1988).

27.) Xu, L., ET AL., "Effects of Local Anesthetics on Single Channel Behavior of Skeletal Muscle Calcium Release Channel." J. GEN. PHYSIOL. 101(2): 207-233 (1993).

28.) Valdivia, H. H., ET AL., "Direct Binding of Verapamil to the Ryanodine Receptor Channel of Sarcoplasmic Reticulum." BIOPHYS J. 58(2): 471-481 (1990).

29.) Honen, B. N., ET AL., "Suppression of Calcium Sparks in Rat Ventricular Myocytes and Direct Inhibition of Sheep Cardiac RyR Channels by EPA, DHA and Oleic Acid." J. MEMBR. BIOL. 196(2): 95-103 (2003).

30.) Sato T., ET AL., "Bepridil, an Antiarrhythmic Drug, Opens Mitochondrial KATP Channels, Blocks Sarcolemmal KATP Channels, and Confers Cardioprotection." J. PHARMACOL. EXP. THER. 316: 182-188 (2006).

31.) Gill, A., ET AL., "Pharmacology of Bepridil." AM. J. CARDIOL. 69(11):11D-16D (1992).

32.) Stark, U., ET AL., "Rate-Dependent Effects of Detajmium and Propafenone on Ventricular Conduction and Refractoriness in Isolated Guinea Pig Hearts." J. CARDIOVASC. PHARMACOL. 27(1): 125-131 (1996).

33.) Quan, C., ET AL., "Use-Dependent Inhibition of Na+ Currents by Benzocaine Homologs." BIOPHYS. J. 70(1): 194-201 (1996).

34.) MacLennan, D. H., "Purification and Properties of an Adenosine Triphosphatase from Sarcoplasmic Reticulum." J. BIOL. CHEM. 245(17): 4508-4518 (1970).

35.) Roubaud, V., ET AL., "Quantitative Measurement of Superoxide Generation Using the Spin Trap 5-(diethoxyphosphoryl)-5-methyl-1-pyrroline-N-oxide." ANAL. BIOCHEM. 247(2): 404-411 (1997).

36.) Sanders, S. P., ET AL., "A Comparative Study of EPR Spin Trapping and Cytochrome C Reduction Techniques for the Measurement of Superoxide Anions." FREE RADIC. BIOL. MED. 16(6): 753-761 (1994).

37.) Jiang, M. and Zhang, J., "Water Stress-Induced Abscisic Acid Accumulation Triggers the Increased Generation of Reactive Oxygen Species and Up-Regulates the Activities of Antioxidant Enzymes in Maize Leaves." J. EXP. BOT. 53(379): 2401-2410 (2002).

38.) Carballal, S., ET AL., "Sulfenic Acid Formation in Human Serum Albumin by Hydrogen Peroxide and Peroxynitrite." BIOCHEMISTRY 42(33): 9906-9914 (2003).

39.) Ellis, H. R. and Poole, L. B., "Novel Application of 7-chloro-4-nitrobenzo-2-oxa-1,3-diazole to Identify Cysteine Sulfenic Acid in the AhpC Component of Alkyl Hydroperoxide Reductase." BIOCHEMISTRY 36(48): 15013-15018 (1997).

40.) Aboderin, A. A. and Boedefeld, E., "Reaction of Chicken Egg White Lysozyme with 7-chloro-4-nitrobenz-2-oxa-1,3-diazole. II. Sites of Modification." BIOCHIM. BIOPHYS. ACTA 420(1): 177-186 (1976).

41.) Sutherland, M. W., and Learmonth, B. A., "The Tetrazolium Dyes MTS and XTT Provide New Quantitative Assays for Superoxide and Superoxide Dismutase." FREE RADIC. RES. 27(3): 283-289 (1997).

42.) Olojo, R. O., ET AL., "Spectrophotometric and fluorometric assay of superoxide ion using 4-chloro-7-nitrobenzo-2-oxa-1,3-diazole." ANALYTICAL BIOCHEM. 339: 338-344 (2005).

We claim:

1. A method for identifying the redox activity of a subject compound, comprising:
   forming an aerobic mixture comprising a free-radical precursor and a subject compound;
   converting the free-radical precursor into a free-radical anion and a free-radical cation; and
   identifying the redox activity of the subject compound.

2. The method according to claim 1, wherein converting the free-radical precursor into a free-radical anion and a free-radical cation comprises exposing the free-radical precursor to light.

3. The method according to claim 1, wherein the subject compound is an electron acceptor and the mixture further comprises an initial electron donor to donate an electron to the free-radical cation.

4. The method according to claim 1, further comprising identifying the level of biological activity of the subject compound based on its redox activity.

5. The method according to claim 1, further comprising measuring superoxide concentration in the mixture.

6. The method according to claim 5, wherein the mixture further comprises a superoxide detection molecule that reacts with superoxide to form a detectable product.

7. The method according to claim 6, wherein measuring the concentration of superoxide in the mixture comprises measuring a concentration of the detectable product.

8. The method according to claim 7, wherein measuring the concentration of the detectable product comprises measuring light absorbance at a wavelength absorbed by the detectable product or light fluorescence at a wavelength emitted by the detectable product.

9. The method according to claim 6, wherein the superoxide detection molecule is NBD-Cl, XTT, a derivative thereof, or a combination thereof.

10. The method according to claim 7, wherein the superoxide detection molecule is NBD-Cl or XTT and measuring the concentration of the detectable product comprises measuring light absorbance at a wavelength of about 470 nm.

11. The method according to claim 7, wherein the superoxide detection molecule is NBD-Cl and measuring the concentration of the detectable product comprises measuring light fluorescence at an excitation wavelength of about 470 nm and an emission wavelength of about 550 nm.

12. The method according to claim 6, wherein the superoxide detection molecule is NBD-Cl and the concentration of NBD-Cl in the mixture prior to reaction with superoxide is between about 30 µM and about 500 µM.

13. The method according to claim 1, further comprising measuring the concentration of the free-radical precursor, the free-radical anion and/or the free-radical cation.

14. The method according to claim 13, wherein the free-radical precursor comprises eosin, erythrosin, methylene blue, or a derivative or combination thereof.

15. The method according to claim 13, wherein measuring the concentration of the free-radical precursor comprises measuring light absorbance at a wavelength absorbed by the free-radical precursor.

16. The method according to claim 15, wherein the free-radical precursor is a dye and the dye bleaches by reaction of two free-radical anion molecules.

17. A method for screening compounds, comprising:
    forming an aerobic mixture comprising a free-radical precursor, a subject compound and a superoxide detection molecule that reacts with superoxide to form a detectable product;
    exposing the free-radical precursor to light to convert the free-radical precursor into a free-radical anion and a free-radical cation;
    measuring the concentration of superoxide in the aerobic mixture by measuring light absorbance at a wavelength absorbed by the detectable product or light fluorescence at a wavelength emitted by the detectable product; and
    screening the subject compound based on its redox activity and/or a biological activity identified based on the redox activity.

18. The method according to claim 6, wherein the superoxide detection molecule has a general formula

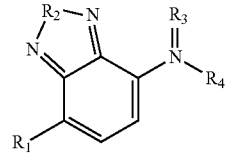

wherein $R_1$ is a halogen, and $R_2$, $R_3$ and $R_4$ independently are oxygen or sulfur.

* * * * *

UNITED STATES PATENT AND TRADEMARK OFFICE
CERTIFICATE OF CORRECTION

PATENT NO. : 8,017,401 B2
APPLICATION NO. : 11/884051
DATED : September 13, 2011
INVENTOR(S) : Abramson et al.

Page 1 of 1

It is certified that error appears in the above-identified patent and that said Letters Patent is hereby corrected as shown below:

In the Specification:

Column 2, line 62, "excitation a wavelength" should read -- excitation wavelength --

Column 3, lines 30-31, "to developing" should read -- to develop --

Column 6, line 57, "can monitored" should read -- can be monitored --

Column 9, line 66, "range about" should read -- range of about --

Column 12, line 25, "1-2 ☐M" should read -- 1-2 µM --

Column 13, line 11, "were carried" should read -- were carried out --

Column 14, line 61, "80g/ml" should read -- 80 µg/ml --

Column 16, lines 40-41, "At low a oxygen" should read -- At a low oxygen --

Column 16, line 46, "absence NBD-C1" should read -- absence of NBD-CI --

Column 17, line 46, "H.1™" should read -- H.1TM --

Signed and Sealed this
First Day of May, 2012

David J. Kappos
*Director of the United States Patent and Trademark Office*